United States Patent [19]

Kehne et al.

[11] Patent Number: 5,223,017
[45] Date of Patent: Jun. 29, 1993

[54] SUBSTITUTED SULFONYLALKYLSULFONYLUREAS AND THEIR USE AS HERBICIDES AND PLANT GROWTH REGULATORS

[75] Inventors: Heinz Kehne, Hofheim am Taunus; Lothar Willms, Hillscheid; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 725,564

[22] Filed: Jul. 3, 1991

[30] Foreign Application Priority Data

Jul. 6, 1990 [DE] Fed. Rep. of Germany ....... 4021489

[51] Int. Cl.$^5$ ................. C07D 239/42; C07D 401/12; C07D 403/12; A01N 43/54

[52] U.S. Cl. .................... 504/214; 544/320; 544/321; 544/323; 544/332; 544/295; 544/122; 544/123; 544/58.60; 504/215; 504/212; 504/213; 504/211; 504/178; 504/167; 504/168; 504/169; 504/170; 504/181

[58] Field of Search ........... 71/92, 90; 544/320, 544/321, 323, 332, 295, 122, 123, 58.6

[56] References Cited

U.S. PATENT DOCUMENTS

| | | | |
|---|---|---|---|
| 3,862,184 | 1/1975 | Goralski et al. | 260/247.1 R |
| 3,865,822 | 2/1975 | Goralski et al. | 260/247.1 R |
| 3,946,007 | 3/1976 | Goralski et al. | 260/247.1 R |
| 4,419,121 | 12/1992 | Meyer et al. | 71/92 |
| 4,443,243 | 4/1984 | Fory et al. | 71/93 |

FOREIGN PATENT DOCUMENTS

| | | |
|---|---|---|
| 0061661 | 10/1982 | European Pat. Off. . |
| 0085236 | 12/1982 | European Pat. Off. . |
| 0070698 | 1/1983 | European Pat. Off. . |
| 0071958 | 2/1983 | European Pat. Off. . |
| 0085276 | 8/1983 | European Pat. Off. . |
| 0131258 | 1/1985 | European Pat. Off. . |
| 0237292 | 9/1987 | European Pat. Off. . |
| 0252640 | 1/1988 | European Pat. Off. . |
| 0336354 | 10/1989 | European Pat. Off. . |
| 0347788 | 12/1989 | European Pat. Off. . |
| 0353641 | 2/1990 | European Pat. Off. . |

OTHER PUBLICATIONS

Beilsteins Handbuch Der Organischen Chemie, 1928, p. 304.
Beilsteins Handbuch Der Organischen Chemie, 1959, pp. 2654, 2690.
Synthesis Communications, Dec. 1986, pp. 1031–1032, The Reaction of Sulfinic Acid Salts with Hydroxylamine-O-sulfonic Acid, A Useful Synthesis of Primary Sulfonamides Graham.

Primary Examiner—John M. Ford
Attorney, Agent, or Firm—Curtis, Morris & Safford

[57] ABSTRACT

Compounds of formula (I) or salts thereof,

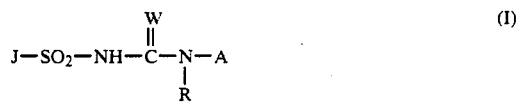

in which J is a radical of the formula $R^1SO_2—CR^2R^3—$, $R^4R^5N—SO_2—CR^2R^3—$, or

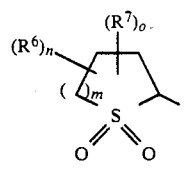

or

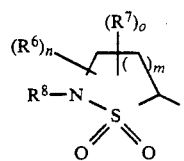

and wherein the radicals $R^1$, $R^2$, $R^3$, $R^6$, $R^7$, $R^8$, $R^*$, A, W, m, n and 0 are defined as set forth in the specification, are suitable as selective herbicides and plant growth regulators.

13 Claims, No Drawings

SUBSTITUTED SULFONYLALKYLSULFONYLUREAS AND THEIR USE AS HERBICIDES AND PLANT GROWTH REGULATORS

It has been disclosed that substituted alkylsulfonylureas have herbicidal and plant-growth-regulating properties (EP 61,661 (U.S. Pat. No. 4,440,565), EP 71,958 (U.S. Pat. No. 4,492,598), EP 85,236, EP 336,354 (ZA 89/2495)).

However, the actions of these compounds are not always satisfactory.

Heterocyclically substituted sulfonylalkylsulfonylureas which are particularly suitable as herbicides and plant growth regulators have now been found.

The present invention therefore relates to compounds of the formula (I) or salts thereof

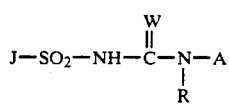
(I)

in which J is a radical of the formula (J-1)-(J-4)

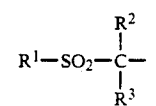
(J-1)

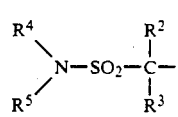
(J-2)

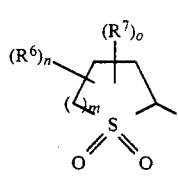
(J-3)

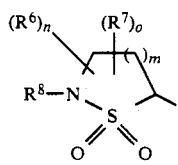
(J-4)

and in these $R^1$ is a saturated or unsaturated, straight-chain or branched hydrocarbon radical which is unsubstituted or mono- or polysubstituted by radicals from the group comprising halogen, alkoxy, alkylthio and alkoxycarbonyl, or is phenyl or phenylalkyl, the phenyl radical in each case being unsubstituted or monosubstituted or polysubstituted by radicals from the group comprising halogen, alkyl, alkoxy, alkylthio, alkylsulfinyl, alkylsulfonyl, alkoxycarbonyl and radicals which are analogous to the 6 last-mentioned radicals and which are monohalogenated or polyhalogenated in the alkyl moiety, $R^2$ and $R^3$ independently of one another are hydrogen, halogen, alkoxy, alkylthio, alkyl, alkenyl or alkynyl, the 5 last-mentioned radicals being unsubstituted or monosubstituted or polysubstituted by halogen, alkoxy or alkylthio, or alkoxycarbonylalkyl, phenyl or phenylalkyl, and the phenyl radical in each case being unsubstituted or substituted by one or more radicals from the group comprising halogen, alkyl, alkoxy, alkoxycarbonyl, alkylthio and alkylsulfonyl, the 5 last-mentioned radicals being unsubstituted or monohalogenated or polyhalogenated in the alkyl moiety, $R^4$ and $R^5$ independently of one another are hydrogen, alkyl, alkenyl or alkynyl, the 3 last-mentioned radicals being unsubstituted or monosubstituted or polysubstituted by radicals from the group comprising halogen, alkoxy and alkylthio, or are alkoxycarbonylalkyl, phenyl or phenylalkyl, the phenyl radical in the 2 last-mentioned radicals being unsubstituted or monosubstituted or polysubstituted by radicals from the group comprising halogen, alkyl, alkoxy, alkylthio, alkylsulfonyl, the 4 abovementioned radicals being unsubstituted in the alkyl moiety or monohalogenated or polyhalogenated, and alkoxycarbonyl, or are dialkylamino or alkoxy, or $R^4$ and $R^5$ together with the N atom linking them are a heterocyclic ring which has 3 to 8 ring atoms and which, besides the N atom, can contain further hetero atoms from the group comprising N, O and S in the ring and which can further be substituted by one or more radicals from the group comprising alkyl, alkoxycarbonyl and alkoxyalkyl, $R^6$ and $R^7$ independently of one another are halogen, alkyl, alkenyl, alkynyl or alkoxy, the 4 last-mentioned radicals being unsubstituted or monosubstituted or polysubstituted by radicals from the group comprising halogen, alkoxy and alkylthio, or are alkoxycarbonylalkyl, $R^8$ is hydrogen, alkyl, alkenyl, alkynyl or alkoxy, the 4 last-mentioned radicals being unsubstituted or monosubstituted or polysubstituted by radicals from the group comprising halogen, alkoxy and alkylthio, or is alkoxycarbonylalkyl, $R^9$ and $R^{10}$ independently of one another are hydrogen, alkyl, alkenyl, alkynyl or alkoxy, the 4 last-mentioned radicals being unsubstituted or monosubstituted or polysubstituted by radicals from the group comprising halogen, alkoxy and alkylthio, or are alkoxycarbonylalkyl, or $R^9$ and $R^{10}$ together with the N atom linking them are a heterocyclic ring which has 3 to 8 ring atoms and which can, besides the N atom, furthermore contain hetero atoms from the group comprising N, O and S, and which can be substituted by alkyl, m is 1, 2 or 3, n and o independently of one another are 0, 1, 2 or 3, A is a radical of the formulae (A-1) to (A-8)

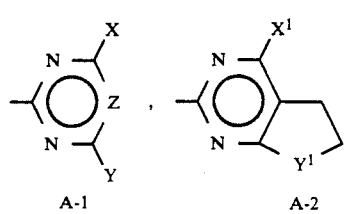

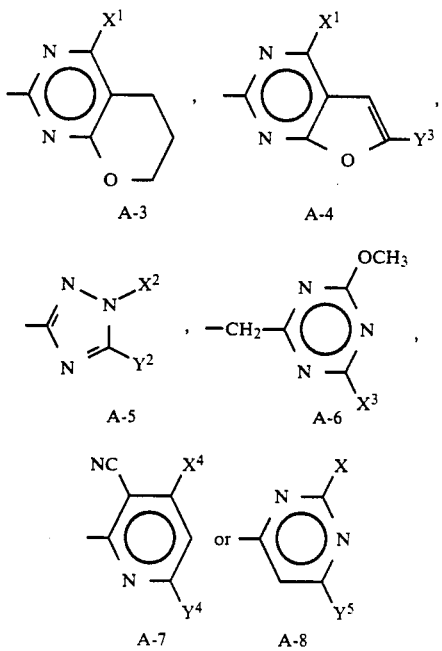

X and Y independently of one another are H, halogen, alkyl, alkoxy or alkylthio, the abovementioned alkyl-containing radicals being unsubstituted or monosubstituted or polysubstituted by radicals from the group comprising halogen, alkoxy and alkylthio, or are a radical of the formula $NR^9R^{10}$, cycloalkyl, alkenyl, alkynyl, alkenyloxy or alkynyloxy, Z is CH or N, $X^1$ is alkyl, alkoxy, haloalkyl or haloalkoxy, $Y^1$ is —O— or —$CH_2$—, $X^2$ is alkyl or haloalkyl, $Y^2$ is alkyl, alkoxy or alkylthio, $X^3$ is alkyl or alkoxy, $Y^3$ is H or alkyl, $X^4$ is alkyl, alkoxy, alkoxyalkyl or halogen, $Y^4$ is alkyl, alkoxy or halogen, $Y^5$ is alkyl, alkoxy or halogen, W is O or S and R is hydrogen or alkyl.

In formula (I), alkyl, alkoxy, haloalkyl, alkylamino and alkylthio radicals and the corresponding unsaturated and/or substituted radicals in the alkyl moiety can in each case be straight-chain or branched. Alkyl radicals, also in the compound meanings such as alkoxy, haloalkyl, alkylthio, alkoxycarbonyl etc, are, unless specified in greater detail, preferably methyl, ethyl, n- or i-propyl, n-, i-, t- or 2-butyl, pentyl such as n- or i-pentyl, hexyl such as n-, i- and 2-hexyl; cycloalkyl is generally $C_3$-$C_5$-cycloalkyl; alkenyl and alkynyl radicals have the meaning of the unsaturated radicals which are possible and which correspond to the alkyl radicals, such as 2-propenyl, 2- or 3-butenyl, 2-propynyl, 2- or 3-butynyl. Halogen is fluorine, chlorine, bromine or iodine.

The compounds of the formula (I) can form salts in which the hydrogen of the —$SO_2$—NH— group is replaced by a cation which is suitable for agriculture. Examples of these salts are metal salts, in particular alkali metal salts or alkaline earth metal salts, and also ammonium salts or salts with organic amines.

The sulfonylureas of the formula (I) which contain one or more asymmetric carbon atoms in the aliphatic radical J can exist in various enantiomeric or diastereoomeric forms. As a rule, the corresponding compounds according to the invention are obtained in the form of racemates or mixtures of diastereometers. If desired, the customary techniques for separating these mixtures into the stereo-chemically uniform components can be used. Synthesis of the pure compounds mentioned is also possible by using stereochemically uniform starting materials.

Formula (I) therefore embraces all abovementioned enantiomeric and diastereomeric forms of the above-defined compounds.

Compounds according to the invention of the abovementioned formula (I), or salts thereof, which are of particular interest are those in which $R^1$ is ($C_1$-$C_6$)alkyl, ($C_2$-$C_6$)alkenyl, ($C_2$-$C_6$)alkynyl, the three last-mentioned radicals being unsubstituted or monosubstituted or polysubstituted by halogen or monosubstituted or disubstituted by radials from the group comprising ($C_1$-$C_4$)alkoxy, ($C_1$-$C_4$)alkylthio and ($C_1$-$C_4$)alkoxycarbonyl, or is —($CH_2$)$_a$-phenyl, a being 0, 1 or 2 and the phenyl radical being unsubstituted or monosubstituted or polysubstituted by radicals from the group comprising halogen, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl and ($C_1$-$C_4$-alkoxy)carbonyl and radicals which are analogous to the 6 last-mentioned radicals and which are monohalogenated or polyhalogenated in the alkyl moiety, $R^2$ and $R^3$ independently of one another are hydrogen, halogen, ($C_1$-$C_4$)alkoxy, ($C_1$-$C_4$)alkylthio, ($C_1$-$C_6$)alkyl, ($C_2$-$C_6$)alkenyl, ($C_2$-$C_6$)alkynyl, the 5 last-mentioned radicals being unsubstituted or monosubstituted or polysubstituted by halogen or monosubstituted or disubstituted by radicals from the group comprising ($C_1$-$C_4$)alkoxy and ($C_1$-$C_4$)alkylthio, or are ($C_1$-$C_4$-alkoxy)carbonyl-($C_1$-$C_3$)alkyl, —($CH_2$)$_a$-phenyl, a being 0, 1 or 2 and the phenyl radical being unsubstituted or substituted by one or more radicals from the group comprising halogen, ($C_1$-$C_4$)alkyl, ($C_1$-$C_4$)alkoxy, ($C_1$-$C_4$-alkoxy)carbonyl, ($C_1$-$C_4$)alkylthio and ($C_1$-$C_4$)alkylsulfonyl, the 5 last-mentioned radicals being unsubstituted in the alkyl moiety or monosubstituted or polysubstituted by halogen, $R^4$ and $R^5$ independently of one another are hydrogen, ($C_1$-$C_8$)alkyl, ($C_2$-$C_8$)alkenyl, ($C_2$-$C_8$)alkynyl, the 3 last-mentioned radicals being unsubstituted or monosubstituted or polysubstituted by halogen or monosubstituted or disubstituted by ($C_1$-$C_4$)alkoxy or ($C_1$-$C_4$)alkylthio, or are ($C_1$-$C_4$-)alkoxycarbonyl-($C_1$-$C_3$)alkyl, —($CH_2$)$_a$-phenyl, a being 0, 1 or 2 and the phenyl radical being unsubstituted or monosubstituted or polysubstituted by radicals from the group comprising halogen, ($C_1$-$C_4$)alkyl, ($C_1$-$C_4$)alkoxy, ($C_1$-$C_4$)alkylthio, ($C_1$-$C_4$)alkylsulfonyl, the 4 above-mentioned radicals being unsubstituted in the alkyl moiety or monosubstituted or polysubstituted by halogen, and ($C_1$-$C_4$-alkoxy)carbonyl, or are ($C_1$-$C_6$)alkoxy or di($C_1$-$C_6$)alkylamino, or $R^4$ and $R^5$ together with the N atom linking them are a heterocyclic ring of the formula

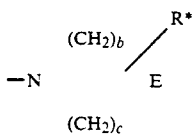

b and c independently of one another being 0, 1, 2 or 3, R* being hydrogen, $(C_1-C_4)$alkyl, $(C_1-C_4$-alkoxy)carbonyl or $(C_1-C_4$-alkoxy)methyl and E being a divalent group of the formula O, S, $CH_2$ or N—$(C_1-C_4)$alkyl, $R^6$ and $R^7$ independently of one another are halogen, $(C_1-C_8)$alkyl, $(C_2-C_8)$alkenyl, $(C_2-C_8)$alkynyl or $(C_1-C_8)$alkoxy, the 4 last-mentioned radicals being unsubstituted or monosubstituted or polysubstituted by halogen or monosubstituted or disubstituted by $(C_1-C_4)$alkoxy or $(C_1-C_4)$alkylthio, or are $(C_1-C_4$-alkoxy)carbonyl-$(C_1-C_3)$alkyl, $R^8$ is hydrogen, $(C_1-C_8)$alkyl, $(C_2-C_8)$alkenyl, $(C_2-C_8)$alkynyl or $(C_1-C_8)$alkoxy, the 4 last-mentioned radicals being unsubstituted or monosubstituted or polysubstituted by halogen or monosubstituted or disubstituted by $(C_1-C_4)$alkoxy or $(C_1-C_4)$alkylthio, or is $(C_1-C_4$-alkoxy)carbonyl-$(C_1-C_3)$alkyl, $R^9$ is hydrogen, $(C_1-C_8)$alkyl, $(C_2-C_8)$alkenyl, $(C_2-C_8)$alkynyl or $(C_1-C_8)$alkoxy, the 4 last-mentioned radicals being unsubstituted or monosubstituted or polysubstituted by halogen or monosubstituted or disubstituted by $(C_1-C_4)$alkoxy or $(C_1-C_4)$alkylthio, or is $(C_1-C_4$-alkoxy)carbonyl-$(C_1-C_3)$alkyl, $R^{10}$ is hydrogen, $(C_1-C_4)$alkyl, $(C_1-C_4$-alkoxy)carbonyl or $(C_1-C_4$-alkoxy)methyl, m is 1, 2 or 3, preferably 1 or 2, n and o independently of one another are 0, 1, 2 or 3, preferably 0 or 1, A is a radical of the abovementioned formulae (A-1) to (A-8), preferably the formula (A-1), X and Y are H, halogen, $(C_1-C_3)$alkyl, $(C_1-C_3)$alkoxy or $(C_1-C_3)$alkylthio, it being possible for the abovementioned alkyl-containing radicals to be monosubstituted or polysubstituted by halogen or monosubstituted or disubstituted by $(C_1-C_3)$alkoxy or $(C_1-C_3)$alkylthio, furthermore a radical of the formula $NR^9R^{10}$ $(C_3-C_6)$ cycloalkyl, $(C_2-C_4)$alkenyl, $(C_2-C_4)$alkynyl, $(C_3-C_4)$alkenyloxy or $(C_3-C_4)$alkynyloxy, preferably with the proviso that the two radicals together are not simultaneously radicals from the group comprising halogen, alkylthio, radicals of the formula $NR^9R^{10}$, alkenyl and alkynyl, Z is CH or N, preferably CH, $X^1$ is $CH_3$, $OCH_3$, $OC_2H_5$ or $OCF_2H$, $Y^1$ is —O— or —$CH_2$—, $X^2$ is $CH_3$, $C_2H_5$, or $CH_2CF_3$, $Y^2$ is $OCH_3$, $OC_2H_5$, $SCH_5$, $SC_2H_5$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl, $Y^5$ is $CH_3$, $C_2H_5$, $OCH_3$ or Cl, W is O or S and R is hydrogen or $CH_3$.

Preferred compounds of the formula (I) are those in which $R^1$ is $(C_1-C_4)$alkyl, $R^2$ and $R^3$ independently of one another are hydrogen, $(C_1-C_4)$alkyl or $(C_2-C_4)$alkenyl, $R^4$ and $R^5$ independently of one another are hydrogen, $(C_1-C_4)$alkyl, $(C_1-C_4)$alkoxy, $(C_2-C_4)$alkenyl, or $R^4$ and $R^5$ together are a heterocyclic radical of the formula

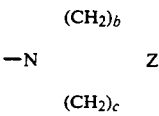

b and independently of one another being 0, 1, 2 or 3, the total of b+c being the number 3 or 4, and Z being O or $CH_2$, $R^6$ and $R^7$ independently of one another are $(C_1-C_3)$-alkyl, $R^8$ is $(C_1-C_4)$alkyl or $(C_2-C_4)$alkenyl, $R^9$ and $R^{10}$ independently of one another are hydrogen or $(C_1-C_4)$alkyl, m is 1 or 2, n and o independently of one another are 0, 1 or 2, preferably 0 or 1, A is a radical of the formula (A-1), X and Y independently of one another are halogen, $(C_1-C_4)$alkyl or $(C_1-C_4)$alkoxy, it being possible for the two last-mentioned radicals to be monosubstituted or polysubstituted by halogen, and W is an oxygen atom.

Other preferred compounds of the formula (I) are those in which J is a radical of the formula J-2 mentioned. Compounds of the formula (I) which contain a combination of the abovementioned preferred characteristics are also preferred.

The present invention furthermore relates to processes for the preparation of compounds of the abovementioned formula (I) or salts thereof, which comprises reacting a) a compound of the formula (II)

$$J-SO_2NH_2 \quad \text{(II)}$$

in which J is as defined in formula (I), with a heterocyclic thio)carbamate of the formula (III)

in which $R^{11}$ is $(C_1-C_5)$alkyl, $(C_1-C_4)$haloalkyl or phenyl which is unsubstituted or monosubstituted or polysubstituted by a radical from the group comprising halogen, $(C_1-C_4)$alkyl and $NO_2$, and A, R and W have the meanings as in formula (I), b) a sulfonyl carbamate of the formula (IV)

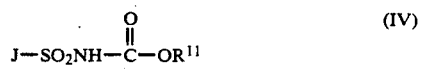

in which $R^{11}$ is as defined under a), with an amino heterocycle of the formula (V),

in which A and R are defined as in formula (I), or c) a sulfonyl isocyanate of the formula (VI)

$$J-SO_2NCO \quad \text{(VI)}$$

in which J is as defined in formula (I), with an amino heterocycle of the formula (V).

The reaction of the compounds of the formulae (II) and (III) is generally catalyzed by bases and carried out in an inert solvent such as, for example, acetonitrile, dioxane, tetrahydrofuran or dichloromethane, at temperatures between 0° C. and the boiling point of the solvent. Suitable as bases are, for example, 1,8-diazabicyclo-[5.4.0]undec-7-ene (DBU) or, in the case of the alkyl carbamates, trimethylaluminum (see EP 70,698).

The sulfonamides (II) are novel compounds. These, and their preparation, are also a subject of this invention. They are obtained, for example, starting from the known compounds of the J-H type by abstracting an α-proton using a strong base such as, for example, butyllithium, reaction of the carbanion with $SO_2$ to give the sulfinate and amination, for example by means of hydroxylamine-O-sulfonic acid (analogously to Synthesis 1986, 1031):

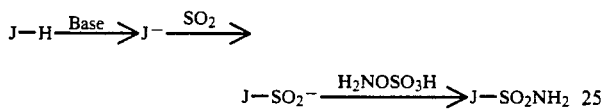

The carbamates of the formula (III) are known from the literature or can be prepared by known processes (EP 70,804 (U.S. Pat. No. 4,443,243), RD 275,056).

The reaction of the compounds (IV) with the amino heterocycles (V) is carried out, for example, in inert, aprotic solvents such as, for example, dioxane, acetonitrile or tetrahydrofuran, at temperatures between 0° C. and the boiling point of the solvent. The starting materials (V) required are known from the literature or can be prepared by processes known from the literature. The sulfonyl carbamates of the formula (IV) are obtained analogously to EP-A-44,808 (U.S. Pat. No. 4,419,121) or EP-A-237,292.

The reaction of the compounds of the formulae (VI) and (V) is carried out, for example, in inert, aprotic solvents such as, for example, acetonitrile, dichloromethane, toluene, tetrahydrofuran or dioxane, at temperatures between 0° C. and the boiling point of the solvent.

The alkylsulfonyl iso(thio)cyanates of the formula (VI) can be prepared in a simple manner by processes known in principle, using the corresponding sulfonamides of the formula (II) (cf. for example, EP 85,276, EP 336,354).

The salts of the compounds of the formula (I) can be prepared, for example, in inert solvents such as, for example, water, methanol or acetone, at temperatures from 0°–100° C. Examples of suitable bases for the preparation of the salts according to the invention are alkali metal carbonates, such as potassium carbonate, alkali metal hydroxides and alkaline earth metal hydroxides, ammonia or ethanolamine.

The compounds of the formula (I) according to the invention have an excellent herbicidal activity against a broad range of economically important monocotyledon and dicotyledon weeds. The active substances act equally well on perennial weeds which produce shoots from rhizomes, rootstocks or other perennial organs and which cannot be easily controlled. In this context, it does not matter whether the substances are applied before sowing, as a pre-emergence treatment or post-emergence treatment. Some representatives of the monocotyledon and dicotyledon weed flora which can be controlled by the compounds according to the invention may be mentioned individually as examples, but this is not to be taken to mean a restriction to certain species.

The monocotyledon weed species controlled include, for example, Avena, Lolium, Alopecurus, Phalaris, Echinochloa, Digitaria and Setaria, and Cyperus species from the annual group, and the perennial species include Agropyron, Cynodon, Imperata and Sorghum, and also perennial Cyperus species.

Of the dicotyledon weed species, the range of action covers species such as, for example, Galium, Viola, Veronica, Lamium, Stellaria, Amaranthus, Sinapis, Ipomoea, Matricaria, Abutilon and Sida from the annual plants, and Convolvulus, Cirsium, Rumex and Artemisia from the perennial weeds.

Excellent control of weeds occurring under the specific culture conditions in rice, such as, for example, Sagittaria, Alisma, Eleocharis, Scirpus and Cyperus, by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely.

When, in the post-emergence method, the active substances are applied to the green parts of the plants, growth also stops dramatically very soon after the treatment, and the weed plants remain in the growth stage of the time of application, or, after a certain period of time, die completely so that competition by the weeds, which is detrimental for the crop plants, is thus eliminated at a very early stage and in a sustained manner.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. For these reasons, the present compounds are very suitable for selectively controlling undesired plant growth in agricultural plantations of useful plants.

In addition, the substances according to the invention have excellent plant growth-regulating properties in crop plants. They engage in the plant metabolism in a regulating manner and can thus be employed for influencing plant components in a targeted fashion and for facilitating harvesting, such as, for example, by provoking desiccation and stunted growth. Furthermore, they are suitable for generally regulating and inhibiting undesired vegetative growth, without simultaneously destroying the plants. Inhibition of vegetative growth plans an important role in many monocotyledon and dicotyledon crops because lodging can be reduced hereby, or prevented completely.

The compounds according to the invention can be employed in the conventional preparations in the form of wettable powders, emulsifiable concentrates, sprayable solutions, dusting agents or granules. The invention therefore also relates to herbicidal and plant-growth-regulating agents which contain the compounds of the formula (I) or salts thereof.

The compounds of the formula (I) can be formulated in various ways, depending on which biological and/or chemicophysical parameters prevail. Examples of formulation possibilities are: wettable powders (WP), water-soluble powders (SP), water-soluble concentrates (SL), emulsifiable concentrates (EC), emulsions (EW) such as oil-in-water and water-in-oil emulsions, sprayable solutions or emulsions, suspension concentrates (SC), dispersions on oil or water base, oil-miscible solutions (OL), suspoemulsions, capsule suspensions (CS), dusting agents (DP), seed-dressing agents, granules for soil application or broadcasting (FG), granules (GR) in the form of microgranules, spray granules, coated granules and absorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986; van Valkenburg, "Pesticides Formulations", Marcel Dekker N.Y., 1973; K. Martens, "Spray Drying Handbook, 3rd Ed. 1979, G. Goodwin Ltd. London.

The formulation auxiliaries required, such as inert materials, surfactants, solvents and other additives, are also known and are described for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schöfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, combinations with other pesticidally active substances, fertilizers and/or growth regulators can also be prepared, for example in the form of a readymix or as a tank mix.

Wettable powders are preparations which are uniformly dispersible in water and which, besides the active substance, also contain wetting agents, for example, polyoxyethylated alkylphenols, polyoxyethylated fatty alcohols and fatty amines, fatty alcohol polyglycol ether sulfates, alkanesulfonates and alkylarylsulfonates, and dispersing agents, for example sodium lignisulfonate, sodium 2,2'-dinaphthylmethane-6,6'-disulfonate, sodium dibutylnaphthalenesulfonate and also sodium oleoylmethyltauride, in addition to a diluent or inert substance.

Emulsifiable concentrates are prepared by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as Ca-dodecylbenzenesulfonate or non-ionic emulsifiers, such as fatty acid polyglycol esters, alkylaryl polyglycol ethers, fatty alcohol polyglycol ethers, propylene oxide/ethylene oxide condensation products (for example block polymers), alkyl polyglycol ethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite or pyrophillite, or diatomaceous earth.

Granules can be produced either by spraying the active substance onto adsorptive, granulated inert material or by applying active substance concentrates onto the surface of carriers such as sand, kaolinites or of granulated inert material, by means of adhesives, for example polyvinyl alcohol, sodium polyacrylate or alternatively mineral oils. Suitable active substances can also be granulated in the manner which is conventional for the production of fertilizer granules, if desired in a mixture with fertilizers.

Disk granules, fluidized-bed granules, extruder granules and spray granules can be prepared by customary processes, see, for example, processes in "Spray-Drying Handbook" 3rd ed. 1979, G. Goodwin Ltd., London; J.E. Browning, "Agglomeration", Chemical and Engineering 1967, pages 147 et seq.; "Perry's Chemical Engineer's Handbook", 5th Ed., McGraw-Hill, New York 1973, p. 8-57.

For further information on the formulation of plant protection agents see, for example, G.C. Klingman, "Weed Control as a Science", John Wiley and Sons, Inc., New York, 1961, pages 81-96 and J.D. Freyer, S.A. Evans, "Weed Control Handbook", 5th Ed., Blackwell Scientific Publications, Oxford, 1968, pages 101-103.

As a rule, the agrochemical preparations contain 0.1 to 99 percent by weight, in particular 0.1 to 95% by weight, of active substance of the formula (I).

The active substance concentration in wettable powders is, for example, about 10 to 90% by weight, the remainder to 100% by weight is composed of conventional formulation components. In the case of emulsifiable concentrates, the active substance concentration can be about 1 to 80% by weight. Formulations in the form of dusts usually contain 1 to 20% by weight of active substance, sprayable solutions about 0.2 to 20% by weight. In the case of granules, the active substance content depends partly on whether the active compound is liquid or solid. The water-dispersible granules usually have a content of between 10 and 90% by weight.

In addition, the active substance formulations mentioned contain, if appropriate, the adhesives, wetting agents, dispersing agents, emulsifiers, penetrants or solvents, fillers or carriers which are conventional in each case.

For use, the formulations, present in commercially available form, are diluted, if appropriate, in a conventional manner, for example using water in the case of wettable powders, emulsifiable concentrates, dispersions and water-dispersible granules. Preparations in the form of dusts, soil granules and granules for broadcasting and also sprayable solutions are usually not further diluted with other inert substances before use.

The application rate required of the compounds of the formula (I) varies with the external conditions, such as temperature, humidity and the type of herbicide used, amongst others. It can vary within wide limits, for example between 0.001 and 10.0 kg/ha or more of active ingredient, but it is preferably between 0.005 and 5 kg/ha.

If appropriate, mixtures or mixed formulations with other active substances, such as, for example, insecticides, acaricides, herbicides, safeners, fertilizers, growth regulators or fungicides are also possible. Such active substances which are suitable for combining are known for example, from "The Pesticide Manual" 9th Edition, British Crop Protection Council 1991, and literature cited therein.

The following examples illustrate the invention in greater detail:

CHEMICAL EXAMPLES

Example 1

3-(4,6-Dimethoxypyrimidin-2-yl)-1-(1-pyrrolidinosulfonylethylsulfonyl)urea a) 1-Pyrrolidinosulfonylethanesulfonamide Under an $N_2$ atmosphere, 68.8 ml (0.11 mol) of a 1.6N solution of n-butyllithium in hexane are added dropwise at −78° C. to 16.3 (0.1 mol) of 1-ethylsulfonylpyrrolidine in 150 ml of absolute tetrahydrofuran. After 6 hours at −78° C., 26.0 g (0.4 mol) of sulfur dioxide are passed in at the same temperature, the mixture is subsequently allowed to come to room temperature, and stirring is continued for 14 hours. Evaporation of the reaction solution gives a crude sulfinate which is dissolved in 300 ml of water without purification. 18.0 g (0.22 mol) of sodium acetate in 20 ml of water and 12.4 g (0.11 mol) of hydroxylamine-O-sulfonic acid in 10 ml of water are added in succession, and the mixture is stirred for 7 hours at room temperature. The water phase is extracted using ethyl acetate, and the organic phase is dried and evaporated. For purification, the crude product obtained in this manner is taken up in 200 ml of 2N sodium hydroxide solution, the water phase is washed 3 times using 100 ml portions of diethyl ether, and the water phase is acidified with hydrochloric acid to pH 2 and extracted using ethyl acetate. After the organic phase has been dried and evaporated, 12.8 g (53% of theory) of 1-pyrrolidinosulfonylethanesulfonamide of melting point 78°–80° C. remain.

b) 3-(4,6-Dimethoxypyrimidin-2-yl)-1-(1-pyrrolidinosulfonylethylsulfonyl)urea

To 3.6 g (0.015 mol) of 1-pyrrolidinosulfonylethanesulfonamide (Example 1a) and 4.0 g (0.019 mol) of phenyl 4,6-dimethoxypyrimidin-2-ylcarbamate in 40 ml of acetonitrile there are added 2.9 g (0.019 mol) of 1,8-diazabicyclo[5.4.0]undec-7-ene (DBU). After the mixture has been stirred for five hours at room temperature, it is treated with 250 ml of ice/water and acidified with HCl to pH 2. Extraction with dichloromethane, drying and evaporation give crude 3-(4,6-dimethoxypyrimidin-2-yl)-1-(1-pyrrolidinosulfonylethylsulfonyl)urea, which is purified by trituration with diisopropyl ether (yield: 4.6 g; 73% of theory; melting point 145°–146° C.).

Example 2

3-(4-Methoxy-6-methyl-1,3,5-triazin-2-yl)-1-(1-pyrrolidinosulfonylethylsulfonyl)urea 9 ml (0.018 mol) of a 2M solution of trimethylaluminum in toluene are added dropwise at room temperature to 3.6 g (0.015 mol) of 1-pyrrolidinosulfonylethanesulfonamide (Example 1a) in 150 ml of dichloromethane. When the evolution of gas has ceased, 3.6 g (0.018 mol) of methyl 4-methoxy-6-methyl-1,3,5-triazin-2-ylcarbamate in 30 ml of dichloromethane are added dropwise, and the resulting solution is refluxed for 24 hours. It is cooled and poured into 150 ml of ice-cold 1N hydrochloric acid. The organic phase is separated off, and the water phase is extracted twice with dichloromethane. The organic phase is dried and evaporated. After the crude product has been triturated with diethyl ether, 2.9 g (47% of theory) of 3-(4-methoxy-6-methyl-1,3,5-triazin-2-yl)-1-(1-pyrrolidinosulfonylethylsulfonyl)urea of melting point 136°–137° C. are obtained.

Example 3

3-(4-chloro-6-methoxypyrimidin-2-yl)-1-(1-pyrrolidinosulfonylethylsulfonyl)urea a) 3-Butyl-1-(1-pyrrolidinosulfonylethylsulfonyl)urea
3.6 g (0.015 mol) of 1-pyrrolidinosulfonylethanesulfonamide (Example 1a) are dissolved in 50 ml of acetone, 2.5 g (0.018 mol) of potassium carbonate are added, and the mixture is stirred for 30 minutes at 50° C. 1.5 g (0.015 mol) of butyl isocyanate are subsequently added dropwise at room temperature, stirring is continued for 5 hours at 50° C., and the solvent is distilled off. The residue is dissolved in water and the mixture is acidified at 0° C. The water phase is extracted with dichloromethane, and the extract is dried and evaporated. After the crude product has been triturated with diisopropyl ether, 3.8 g (74% of theory) of 3-butyl-1-(1-pyrrolidinosulfonylethylsulfonyl)urea of melting point 153°–155° C. are obtained.

b) 1-Pyrrolidinosulfonylethylsulfonyl isocyanate
3.6 g (0.01 mol) of 3-butyl-1-(1-pyrrolidinosulfonylethylsulfonyl)urea (Example 3a) are suspended in 70 ml of xylene; phosgene is subsequently passed in at 130° C. for approximately 2 hours. The solvent is removed in vacuo, and desired sulfonyl isocyanate is obtained in quantitative yield (2.7 g).

c) 3-(4-Chloro-6-methylpyrimidin-2-yl)-1-(1-pyrrolidinosulfonylethylsulfonyl)urea 1.6 g (0.01 mol) of 2-amino-4-chloro-6-methoxypyrimidine are dissolved in 30 ml of dichloromethane, and 2.7 g (0.01 mol) of 1-pyrrolidinosulfonylethylsulfonyl isocyanate (Example 3b) in 30 ml of dichloromethane are added dropwise at room temperature. After the mixture has been stirred for 3 hours at room temperature, the organic phase is washed with 2N HCl and water, dried and evaporated. Trituration of the crude product with diethyl ether gives 30 g (70% of theory) of 3-(4-chloro-6-methoxypyrimidin-2-yl)-1-(1-pyrrolidinosulfonylethylsulfonyl)urea of melting point 158°–160° C.

The compounds defined in Tables 1 to 6 below are obtained analogously.

TABLE 1

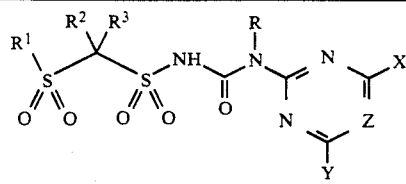

| Compound No. | $R^1$ | $R^2$ | $R^3$ | R | X | Y | Z | M.p. [°C.] |
|---|---|---|---|---|---|---|---|---|
| 4 | $CH_3$ | H | H | H | $OCH_3$ | $OCH_3$ | CH | 185–187 |
| 5 | $CH_3$ | H | H | H | $OCH_3$ | $CH_3$ | CH | |
| 6 | $CH_3$ | H | H | H | $CH_3$ | $CH_3$ | CH | 156–158 |
| 7 | $CH_3$ | H | H | H | $OCH_3$ | Cl | CH | |
| 8 | $CH_3$ | H | H | H | $OCH_3$ | $CH_3$ | N | |
| 9 | $C_2H_5$ | $CH_3$ | H | H | $OCH_3$ | $OCH_3$ | CH | 142–144 |
| 10 | $C_2H_5$ | $CH_3$ | H | H | $OCH_3$ | $CH_3$ | CH | |
| 11 | $C_2H_5$ | $CH_3$ | H | H | $CH_3$ | $CH_3$ | CH | |
| 12 | $C_2H_5$ | $CH_3$ | H | H | $OCH_3$ | Cl | CH | |
| 13 | $C_2H_5$ | $CH_3$ | H | H | $OCH_3$ | $CH_3$ | N | |
| 14 | $C_2H_5$ | $CH_3$ | H | H | $OCH_3$ | $OCH_3$ | N | |
| 15 | $C_2H_5$ | $CH_3$ | H | H | $OCHF_2$ | $OCH_3$ | CH | |
| 16 | $C_2H_5$ | $CH_3$ | H | H | $OCHF_2$ | $OCHF_2$ | CH | |
| 17 | $C_2H_5$ | $CH_3$ | H | H | $OCH_2CF_3$ | $OCH_3$ | N | |
| 18 | $C_2H_5$ | $CH_3$ | H | H | $OC_2H_5$ | $NHCH_3$ | N | |
| 19 | $C_2H_5$ | $CH_3$ | H | H | $CH_3$ | Cl | CH | |
| 20 | $C_2H_5$ | $CH_3$ | H | H | $OC_2H_5$ | $OC_2H_5$ | CH | |
| 21 | $C_2H_5$ | $CH_3$ | H | H | $OCH_3$ | Br | CH | |
| 22 | $C_2H_5$ | $CH_3$ | H | H | $OCH_3$ | $SCH_3$ | CH | |
| 23 | $C_2H_5$ | $CH_3$ | H | H | $OCH_3$ | $OC_3H_7$ | CH | |
| 24 | $C_2H_5$ | $CH_3$ | H | H | $OCH_2CF_3$ | $OCH_3$ | CH | |
| 25 | $C_2H_5$ | $CH_3$ | H | H | $C_2H_5$ | $OCH_3$ | CH | |
| 26 | $C_2H_5$ | $CH_3$ | H | H | $OCH_3$ | $CH(OCH_3)_2$ | CH | |
| 27 | $C_2H_5$ | $CH_3$ | H | $CH_3$ | $OCH_3$ | $OCH_3$ | CH | |
| 28 | $C_2H_5$ | $CH_3$ | H | $CH_3$ | $OCH_3$ | $CH_3$ | N | |
| 29 | $C_3H_7$ | $C_2H_5$ | H | H | $OCH_3$ | $OCH_3$ | CH | |
| 30 | $C_3H_7$ | $C_2H_5$ | H | H | $OCH_3$ | $CH_3$ | CH | |
| 31 | $C_3H_7$ | $C_2H_5$ | H | H | $OCH_3$ | $CH_3$ | N | |
| 32 | $C_4H_9$ | $C_3H_7$ | H | H | $OCH_3$ | $OCH_3$ | CH | |
| 33 | $C_4H_9$ | $C_3H_7$ | H | H | $OCH_3$ | $CH_3$ | CH | |
| 34 | $C_4H_9$ | $C_3H_7$ | H | H | $OCH_3$ | $CH_3$ | N | |
| 35 | $CH_3$ | $CH(CH_3)_2$ | H | H | $OCH_3$ | $OCH_3$ | CH | |
| 36 | $CH_3$ | $CH(CH_3)_2$ | H | H | $OCH_3$ | $CH_3$ | CH | |
| 37 | $CH_3$ | $CH(CH_3)_2$ | H | H | $OCH_3$ | $CH_3$ | N | |
| 38 | $CH_3$ | $CH=CH_2$ | H | H | $OCH_3$ | $OCH_3$ | CH | |
| 39 | $CH_3$ | $CH=CH_2$ | H | H | $OCH_3$ | $CH_3$ | CH | |
| 40 | $CH_3$ | $CH=CH_2$ | H | H | $OCH_3$ | $CH_3$ | N | |
| 41 | $CH_3$ | $C\equiv CCH_3$ | H | H | $OCH_3$ | $OCH_3$ | CH | |
| 42 | $CH_3$ | $C\equiv CCH_3$ | H | H | $OCH_3$ | $CH_3$ | CH | |
| 43 | $CH_3$ | $C\equiv CCH_3$ | H | H | $OCH_3$ | $CH_3$ | N | |
| 44 | $CH_3$ | $C_6H_5$ | H | H | $OCH_3$ | $OCH_3$ | CH | |
| 45 | $CH_3$ | $C_6H_5$ | H | H | $OCH_3$ | $CH_3$ | CH | |
| 46 | $CH_3$ | $C_6H_5$ | H | H | $OCH_3$ | $CH_3$ | N | |
| 47 | $CH_3$ | $CH_3$ | H | H | $OCH_3$ | $OCH_3$ | CH | |
| 48 | $CH_3$ | $CH_3$ | H | H | $OCH_3$ | $CH_3$ | CH | |
| 49 | $CH_3$ | $CH_3$ | H | H | $OCH_3$ | $CH_3$ | N | |
| 50 | $C_3H_7$ | $CH_3$ | H | H | $OCH_3$ | $OCH_3$ | CH | |
| 51 | $C_3H_7$ | $CH_3$ | H | H | $OCH_3$ | $CH_3$ | CH | |
| 52 | $C_3H_7$ | $CH_3$ | H | H | $OCH_3$ | $CH_3$ | N | |
| 53 | $C_6H_{13}$ | $CH_3$ | H | H | $OCH_3$ | $OCH_3$ | CH | |
| 54 | $C_6H_{13}$ | $CH_3$ | H | H | $OCH_3$ | $CH_3$ | CH | |
| 55 | $C_6H_{13}$ | $CH_3$ | H | H | $OCH_3$ | $CH_3$ | N | |
| 56 | $CH(CH_3)_2$ | $CH_3$ | $CH_3$ | H | $OCH_3$ | $OCH_3$ | CH | |
| 57 | $CH(CH_3)_2$ | $CH_3$ | $CH_3$ | H | $OCH_3$ | $CH_3$ | CH | |
| 58 | $CH(CH_3)_2$ | $CH_3$ | $CH_3$ | H | $OCH_3$ | $CH_3$ | N | |
| 59 | $C_6H_5$ | $CH_3$ | H | H | $OCH_3$ | $OCH_3$ | CH | |
| 60 | $C_6H_5$ | $CH_3$ | H | H | $OCH_3$ | $CH_3$ | CH | |
| 61 | $C_6H_5$ | $CH_3$ | H | H | $OCH_3$ | $CH_3$ | N | |
| 62 | $CF_3$ | $CH_3$ | H | H | $OCH_3$ | $OCH_3$ | CH | |
| 63 | $CF_3$ | $CH_3$ | H | H | $OCH_3$ | $CH_3$ | CH | |
| 64 | $CF_3$ | $CH_3$ | H | H | $OCH_3$ | $CH_3$ | N | |
| 65 | $CF_2CHF_2$ | $CH_3$ | H | H | $OCH_3$ | $OCH_3$ | CH | |
| 66 | $CF_2CHF_2$ | $CH_3$ | H | H | $OCH_3$ | $CH_3$ | CH | |
| 67 | $CF_2CHF_2$ | $CH_3$ | H | H | $OCH_3$ | $CH_3$ | N | |
| 68 | $CH_2CH=CH_2$ | $CH_3$ | H | H | $OCH_3$ | $OCH_3$ | CH | |
| 69 | $CH_2CH=CH_2$ | $CH_3$ | H | H | $OCH_3$ | $CH_3$ | CH | |
| 70 | $CH_2CH=CH_2$ | $CH_3$ | H | H | $OCH_3$ | $CH_3$ | N | |
| 71 | $CH_2C\equiv CCH_3$ | $CH_3$ | H | H | $OCH_3$ | $OCH_3$ | CH | |
| 72 | $CH_2C\equiv CCH_3$ | $CH_3$ | H | H | $OCH_3$ | $CH_3$ | CH | |
| 73 | $CH_2C\equiv CCH_3$ | $CH_3$ | H | H | $OCH_3$ | $CH_3$ | N | |

TABLE 1-continued

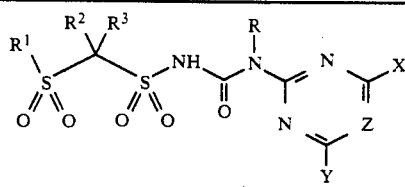

| Compound No. | R¹ | R² | R³ | R | X | Y | Z | M.p. [°C.] |
|---|---|---|---|---|---|---|---|---|
| 74 | CH₃ | CH₃ | CH₃ | H | OCH₃ | OCH₃ | CH | |
| 75 | CH₃ | CH₃ | CH₃ | H | OCH₃ | CH₃ | CH | |
| 76 | CH₃ | CH₃ | CH₃ | H | OCH₃ | CH₃ | N | |
| 77 | CH₃ | CH₃ | C₂H₅ | H | OCH₃ | OCH₃ | CH | |
| 78 | CH₃ | CH₃ | C₂H₅ | H | OCH₃ | CH₃ | CH | |
| 79 | CH₃ | CH₃ | C₂H₅ | H | OCH₃ | CH₃ | N | |
| 80 | CH₃ | CH₃ | C₄H₉ | H | OCH₃ | OCH₃ | CH | |
| 81 | CH₃ | CH₃ | C₄H₉ | H | OCH₃ | CH₃ | CH | |
| 82 | CH₃ | CH₃ | C₄H₉ | H | OCH₃ | CH₃ | N | |
| 83 | CH₃ | C₂H₅ | C₂H₅ | H | OCH₃ | OCH₃ | CH | |
| 84 | CH₃ | C₂H₅ | C₂H₅ | H | OCH₃ | CH₃ | CH | |
| 85 | CH₃ | C₂H₅ | C₂H₅ | H | OCH₃ | CH₃ | N | |

TABLE 2

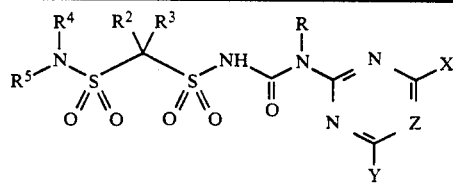

| Compound No. | R⁴ | R⁵ | R² | R³ | R | X | Y | Z | M.p. [°C.] |
|---|---|---|---|---|---|---|---|---|---|
| 86 | CH₃ | CH₃ | H | H | H | OCH₃ | OCH₃ | CH | 200-201 |
| 87 | CH₃ | CH₃ | H | H | H | OCH₃ | CH₃ | CH | |
| 88 | CH₃ | CH₃ | H | H | H | CH₃ | CH₃ | CH | |
| 89 | CH₃ | CH₃ | H | H | H | OCH₃ | Cl | CH | |
| 90 | CH₃ | CH₃ | H | H | H | OCH₃ | CH₃ | N | |
| 91 | CH₃ | CH₃ | CH₃ | H | H | OCH₃ | OCH₃ | CH | 137-140 |
| 92 | CH₃ | CH₃ | CH₃ | H | H | OCH₃ | CH₃ | CH | |
| 93 | CH₃ | CH₃ | CH₃ | H | H | CH₃ | CH₃ | CH | |
| 94 | CH₃ | CH₃ | CH₃ | H | H | OCH₃ | Cl | CH | |
| 95 | CH₃ | CH₃ | CH₃ | H | H | OCH₃ | CH₃ | N | |
| 96 | CH₃ | CH₃ | CH₃ | H | H | OCH₃ | OCH₃ | N | |
| 97 | CH₃ | CH₃ | CH₃ | H | H | OCHF₂ | OCH₃ | CH | |
| 98 | CH₃ | CH₃ | CH₃ | H | H | OCHF₂ | OCHF₂ | CH | |
| 99 | CH₃ | CH₃ | CH₃ | H | H | OCH₂CF₃ | OCH₃ | N | |
| 100 | CH₃ | CH₃ | CH₃ | H | H | OC₂H₅ | NHCH₃ | N | |
| 101 | CH₃ | CH₃ | CH₃ | H | H | CH₃ | Cl | CH | |
| 102 | CH₃ | CH₃ | CH₃ | H | H | OC₂H₅ | OC₂H₅ | CH | |
| 103 | CH₃ | CH₃ | CH₃ | H | H | OCH₃ | Br | CH | |
| 104 | CH₃ | CH₃ | CH₃ | H | H | OCH₃ | SCH₃ | CH | |
| 105 | CH₃ | CH₃ | CH₃ | H | H | OCH₃ | OC₃H₇ | CH | |
| 106 | CH₃ | CH₃ | CH₃ | H | H | OCH₂CF₃ | OCH₃ | CH | |
| 107 | CH₃ | CH₃ | CH₃ | H | H | C₂H₅ | OCH₃ | CH | |
| 108 | CH₃ | CH₃ | CH₃ | H | H | OCH₃ | CH(OCH₃)₂ | CH | |
| 109 | CH₃ | CH₃ | CH₃ | H | CH₃ | OCH₃ | OCH₃ | CH | |
| 110 | CH₃ | CH₃ | CH₃ | H | CH₃ | OCH₃ | CH₃ | N | |
| 111 | CH₃ | CH₃ | C₂H₅ | H | H | OCH₃ | OCH₃ | CH | 122-124 |
| 112 | CH₃ | CH₃ | C₂H₅ | H | H | OCH₃ | CH₃ | CH | |
| 113 | CH₃ | CH₃ | C₂H₅ | H | H | CH₃ | CH₃ | CH | |
| 114 | CH₃ | CH₃ | C₂H₅ | H | H | OCH₃ | Cl | CH | |
| 115 | CH₃ | CH₃ | C₂H₅ | H | H | OCH₃ | CH₃ | N | |
| 116 | CH₃ | CH₃ | C₂H₅ | H | H | OCH₃ | OCH₃ | N | |
| 117 | CH₃ | CH₃ | C₂H₅ | H | H | OCHF₂ | OCH₃ | CH | |
| 118 | CH₃ | CH₃ | C₂H₅ | H | H | OCHF₂ | OCHF₂ | CH | |
| 119 | CH₃ | CH₃ | C₂H₅ | H | H | OCH₂CF₃ | OCH₃ | N | |
| 120 | CH₃ | CH₃ | C₂H₅ | H | H | OC₂H₅ | NHCH₃ | N | |
| 121 | CH₃ | CH₃ | C₂H₅ | H | H | CH₃ | Cl | CH | |
| 122 | CH₃ | CH₃ | C₂H₅ | H | H | OC₂H₅ | OC₂H₅ | CH | |
| 123 | CH₃ | CH₃ | C₂H₅ | H | H | OCH₃ | Br | CH | |
| 124 | CH₃ | CH₃ | C₂H₅ | H | H | OCH₃ | SCH₃ | CH | |
| 125 | CH₃ | CH₃ | C₂H₅ | H | H | OCH₃ | OC₃H₇ | CH | |
| 127 | CH₃ | CH₃ | C₂H₅ | H | H | C₂H₅ | OCH₃ | CH | |
| 128 | CH₃ | CH₃ | C₂H₅ | H | H | OCH₃ | CH(OCH₃)₂ | CH | |

TABLE 2-continued

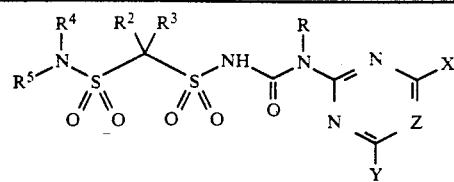

| Compound No. | R⁴ | R⁵ | R² | R³ | R | X | Y | Z | M.p. [°C.] |
|---|---|---|---|---|---|---|---|---|---|
| 129 | CH₃ | CH₃ | C₂H₅ | H | CH₃ | OCH₃ | OCH₃ | CH | |
| 130 | CH₃ | CH₃ | C₂H₅ | H | CH₃ | OCH₃ | CH₃ | N | |
| 131 | CH₃ | CH₃ | C₃H₇ | H | H | OCH₃ | OCH₃ | CH | 105 |
| 132 | CH₃ | CH₃ | C₃H₇ | H | H | OCH₃ | CH₃ | CH | |
| 133 | CH₃ | CH₃ | C₃H₇ | H | H | OCH₃ | CH₃ | N | |
| 134 | CH₃ | CH₃ | C₄H₉ | H | H | OCH₃ | OCH₃ | CH | |
| 135 | CH₃ | CH₃ | C₄H₉ | H | H | OCH₃ | CH₃ | CH | |
| 136 | CH₃ | CH₃ | C₄H₉ | H | H | OCH₃ | CH₃ | N | |
| 137 | CH₃ | CH₃ | CH(CH₃)₂ | H | H | OCH₃ | OCH₃ | CH | |
| 138 | CH₃ | CH₃ | CH(CH₃)₂ | H | H | OCH₃ | CH₃ | CH | |
| 139 | CH₃ | CH₃ | CH(CH₃)₂ | H | H | OCH₃ | CH₃ | N | |
| 140 | CH₃ | CH₃ | CH₂CH=CH₂ | H | H | OCH₃ | OCH₃ | CH | |
| 141 | CH₃ | CH₃ | CH₂CH=CH₂ | H | H | OCH₃ | CH₃ | CH | |
| 142 | CH₃ | CH₃ | CH₂CH=CH₂ | H | H | OCH₃ | CH₃ | N | |
| 143 | CH₃ | CH₃ | CH=CH₂ | H | H | OCH₃ | OCH₃ | CH | |
| 144 | CH₃ | CH₃ | CH=CH₂ | H | H | OCH₃ | CH₃ | CH | |
| 145 | CH₃ | CH₃ | CH=CH₂ | H | H | OCH₃ | CH₃ | N | |
| 146 | CH₃ | CH₃ | C≡CCH₃ | H | H | OCH₃ | OCH₃ | CH | |
| 147 | CH₃ | CH₃ | C≡CCH₃ | H | H | OCH₃ | CH₃ | CH | |
| 148 | CH₃ | CH₃ | C≡CCH₃ | H | H | OCH₃ | CH₃ | N | |
| 149 | CH₃ | CH₃ | CF₃ | H | H | OCH₃ | OCH₃ | CH | |
| 150 | CH₃ | CH₃ | CF₃ | H | H | OCH₃ | CH₃ | CH | |
| 151 | CH₃ | CH₃ | C₆H₅ | H | H | CH₃ | CH₃ | CH | 190–191 |
| 152 | CH₃ | CH₃ | C₆H₅ | H | H | OCH₃ | OCH₃ | CH | 167–169 |
| 153 | CH₃ | CH₃ | C₆H₅ | H | H | OCH₃ | CH₃ | CH | |
| 154 | CH₃ | CH₃ | C₆H₅ | H | H | OCH₃ | CH₃ | N | |
| 155 | CH₃ | CH₃ | CH₃ | CH₃ | H | OCH₃ | OCH₃ | CH | 183 |
| 156 | CH₃ | CH₃ | CH₃ | CH₃ | H | OCH₃ | CH₃ | CH | |
| 157 | CH₃ | CH₃ | CH₃ | CH₃ | H | OCH₃ | CH₃ | N | |
| 158 | CH₃ | CH₃ | C₂H₅ | C₂H₅ | H | OCH₃ | OCH₃ | CH | |
| 159 | CH₃ | CH₃ | C₂H₅ | C₂H₅ | H | OCH₃ | CH₃ | CH | |
| 160 | CH₃ | CH₃ | C₂H₅ | C₂H₅ | H | OCH₃ | CH₃ | N | |
| 161 | CH₃ | C₂H₅ | CH₃ | H | H | OCH₃ | OCH₃ | CH | |
| 162 | CH₃ | C₂H₅ | CH₃ | H | H | OCH₃ | CH₃ | CH | |
| 163 | CH₃ | C₂H₅ | CH₃ | H | H | OCH₃ | CH₃ | N | |
| 164 | CH₃ | C₂H₅ | C₂H₅ | H | H | OCH₃ | OCH₃ | CH | |
| 165 | CH₃ | C₂H₅ | C₂H₅ | H | H | OCH₃ | CH₃ | CH | |
| 166 | CH₃ | C₂H₅ | C₂H₅ | H | H | OCH₃ | CH₃ | N | |
| 167 | C₂H₅ | C₂H₅ | CH₃ | H | H | OCH₃ | OCH₃ | CH | 123–124 |
| 168 | C₂H₅ | C₂H₅ | CH₃ | H | H | OCH₃ | CH₃ | CH | 138–139 |
| 169 | C₂H₅ | C₂H₅ | CH₃ | H | H | OCH₃ | CH₃ | N | 123 (Decomp.) |
| 170 | C₂H₅ | C₂H₅ | C₂H₅ | H | H | OCH₃ | OCH₃ | CH | |
| 171 | C₂H₅ | C₂H₅ | C₂H₅ | H | H | OCH₃ | CH₃ | CH | |
| 172 | C₂H₅ | C₂H₅ | C₂H₅ | H | H | OCH₃ | CH₃ | N | |
| 173 | CH₃ | C₄H₉ | CH₃ | H | H | OCH₃ | OCH₃ | CH | |
| 174 | CH₃ | C₄H₉ | CH₃ | H | H | OCH₃ | CH₃ | CH | |
| 175 | CH₃ | C₄H₉ | CH₃ | H | H | OCH₃ | CH₃ | N | |
| 176 | CH₃ | C₄H₉ | C₂H₅ | H | H | OCH₃ | OCH₃ | CH | |
| 177 | CH₃ | C₄H₉ | C₂H₅ | H | H | OCH₃ | CH₃ | CH | |
| 178 | CH₃ | C₄H₉ | C₂H₅ | H | H | OCH₃ | CH₃ | N | |
| 179 | —(CH₂)₄— | | CH₃ | H | H | OCH₃ | OCH₃ | N | |
| 180 | —(CH₂)₄— | | CH₃ | H | H | OCH₃ | CH₃ | CH | 151–152 (Decomp.) |
| 181 | —(CH₂)₄— | | CH₃ | H | H | Cl | CH₃ | CH | |
| 182 | —(CH₂)₄— | | C₂H₅ | H | H | OCH₃ | OCH₃ | CH | 129–130 |
| 183 | —(CH₂)₄— | | C₂H₅ | H | H | OCH₃ | CH₃ | CH | 128–129 |
| 184 | —(CH₂)₄— | | C₂H₅ | H | H | OCH₃ | CH₃ | N | 159 |
| 185 | —(CH₂)₄— | | C₃H₇ | H | H | OCH₃ | OCH₃ | CH | |
| 186 | —(CH₂)₄— | | C₃H₇ | H | H | OCH₃ | CH₃ | CH | |
| 187 | —(CH₂)₄— | | C₃H₇ | H | H | OCH₃ | CH₃ | N | |
| 188 | —(CH₂)₄— | | CH₃ | CH₃ | H | OCH₃ | OCH₃ | CH | |
| 189 | —(CH₂)₄— | | CH₃ | CH₃ | H | OCH₃ | CH₃ | CH | |
| 190 | —(CH₂)₄— | | CH₃ | CH₃ | H | OCH₃ | CH₃ | N | |
| 191 | —(CH₂)₅— | | CH₃ | H | H | OCH₃ | OCH₃ | CH | 145–146 |
| 192 | —(CH₂)₅— | | CH₃ | H | H | OCH₃ | CH₃ | CH | 164–165 (D.) |
| 193 | —(CH₂)₅— | | CH₃ | H | H | OCH₃ | CH₃ | N | 128–129 |
| 194 | —(CH₂)₅— | | C₂H₅ | H | H | OCH₃ | OCH₃ | CH | |
| 195 | —(CH₂)₅— | | C₂H₅ | H | H | OCH₃ | CH₃ | CH | |
| 196 | —(CH₂)₅— | | C₂H₅ | H | H | OCH₃ | CH₃ | N | |
| 197 | —(CH₂)₂O(CH₂)₂— | | CH₃ | H | H | OCH₃ | OCH₃ | CH | |

TABLE 2-continued

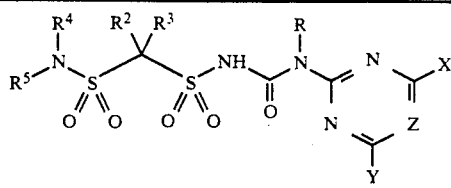

| Compound No. | R⁴ | R⁵ | R² | R³ | R | X | Y | Z | M.p. [°C.] |
|---|---|---|---|---|---|---|---|---|---|
| 198 | —(CH₂)₂O(CH₂)₂— | | CH₃ | H | H | OCH₃ | CH₃ | CH | |
| 199 | —(CH₂)₂O(CH₂)₂— | | CH₃ | H | H | OCH₃ | CH₃ | N | |
| 200 | —(CH₂)₂O(CH₂)₂— | | C₂H₅ | H | H | OCH₃ | OCH₃ | CH | |
| 201 | —(CH₂)₂O(CH₂)₂— | | C₂H₅ | H | H | OCH₃ | CH₃ | CH | |
| 202 | —(CH₂)₂O(CH₂)₂— | | C₂H₅ | H | H | OCH₃ | CH₃ | N | |
| 203 | CH₃ | OCH₃ | CH₃ | H | H | OCH₃ | OCH₃ | CH | |
| 204 | CH₃ | OCH₃ | CH₃ | H | H | OCH₃ | CH₃ | CH | |
| 205 | CH₃ | OCH₃ | CH₃ | H | H | OCH₃ | CH₃ | N | |
| 206 | CH₃ | OCH₃ | C₂H₅ | H | H | OCH₃ | OCH₃ | CH | |
| 207 | CH₃ | OCH₃ | C₂H₅ | H | H | OCH₃ | CH₃ | CH | |
| 208 | CH₃ | OCH₃ | C₂H₅ | H | H | OCH₃ | CH₃ | N | |
| 209 | CH₃ | Allyl | CH₃ | H | H | OCH₃ | OCH₃ | CH | |
| 210 | CH₃ | Allyl | CH₃ | H | H | OCH₃ | CH₃ | CH | |
| 211 | CH₃ | Allyl | CH₃ | H | H | OCH₃ | CH₃ | N | |
| 212 | CH₃ | Allyl | C₂H₅ | H | H | OCH₃ | OCH₃ | CH | |
| 213 | CH₃ | Allyl | C₂H₅ | H | H | OCH₃ | CH₃ | CH | |
| 214 | CH₃ | Allyl | C₂H₅ | H | H | OCH₃ | CH₃ | N | |
| 215 | CH₃ | CH₂CO₂CH₃ | CH₃ | H | H | OCH₃ | OCH₃ | CH | |
| 216 | CH₃ | CH₂CO₂CH₃ | CH₃ | H | H | OCH₃ | CH₃ | CH | |
| 217 | CH₃ | CH₂CO₂CH₃ | CH₃ | H | H | OCH₃ | CH₃ | N | |
| 218 | CH₃ | CH₂CO₂CH₃ | C₂H₅ | H | H | OCH₃ | OCH₃ | CH | |
| 219 | CH₃ | CH₂CO₂CH₃ | C₂H₅ | H | H | OCH₃ | CH₃ | CH | |
| 220 | CH₃ | CH₂CO₂CH₃ | C₂H₅ | H | H | OCH₃ | CH₃ | N | |
| 221 | CH₃ | C₆H₅ | CH₃ | H | H | OCH₃ | OCH₃ | CH | |
| 222 | CH₃ | C₆H₅ | CH₃ | H | H | OCH₃ | CH₃ | CH | |
| 223 | CH₃ | C₆H₅ | CH₃ | H | H | OCH₃ | CH₃ | N | |
| 224 | CH₃ | C₆H₅ | C₂H₅ | H | H | OCH₃ | OCH₃ | CH | |
| 225 | CH₃ | C₆H₅ | C₂H₅ | H | H | OCH₃ | CH₃ | CH | |
| 226 | CH₃ | C₆H₅ | C₂H₅ | H | H | OCH₃ | CH₃ | N | |
| 227 | Allyl | Allyl | CH₃ | H | H | OCH₃ | OCH₃ | CH | |
| 228 | Allyl | Allyl | CH₃ | H | H | OCH₃ | CH₃ | CH | |
| 229 | Allyl | Allyl | CH₃ | H | H | OCH₃ | CH₃ | N | |
| 230 | Allyl | Allyl | C₂H₅ | H | H | OCH₃ | OCH₃ | CH | |
| 231 | Allyl | Allyl | C₂H₅ | H | H | OCH₃ | CH₃ | CH | |
| 232 | Allyl | Allyl | C₂H₅ | H | H | OCH₃ | CH₃ | N | |
| 233 | C₂H₅ | C₂H₅ | CH₃ | H | H | OCH₃ | Cl | CH | |
| 234 | C₂H₅ | C₂H₅ | CH₃ | H | H | CH₃ | CH₃ | CH | |
| 235 | C₂H₅ | C₂H₅ | CH₃ | H | H | OCH₃ | OCH₃ | N | |
| 236 | C₂H₅ | C₂H₅ | C₂H₅ | H | H | OCH₃ | Cl | CH | |
| 237 | C₂H₅ | C₂H₅ | C₂H₅ | H | H | CH₃ | CH₃ | CH | |
| 238 | C₂H₅ | C₂H₅ | C₂H₅ | H | H | OCH₃ | OCH₃ | N | |
| 239 | —(CH₂)₄— | | C₂H₅ | H | H | OCH₃ | Cl | CH | |
| 240 | —(CH₂)₄— | | C₂H₅ | H | H | CH₃ | CH₃ | CH | |
| 241 | —(CH₂)₄— | | C₂H₅ | H | H | OCH₃ | OCH₃ | N | |
| 242 | —(CH₂)₄— | | CH₃ | CH₃ | H | OCH₃ | Cl | CH | |
| 243 | —(CH₂)₄— | | CH₃ | CH₃ | H | CH₃ | CH₃ | CH | |
| 244 | —(CH₂)₄— | | CH₃ | CH₃ | H | OCH₃ | OCH₃ | N | |
| 245 | —(CH₂)₅— | | CH₃ | H | H | OCH₃ | Cl | CH | 135–136 |
| 246 | —(CH₂)₅— | | CH₃ | H | H | CH₃ | CH₃ | CH | 123–125 |
| 247 | —(CH₂)₅— | | CH₃ | H | H | OCH₃ | OCH₃ | N | 125–126 (D.) |
| 248 | —(CH₂)₅— | | C₂H₅ | H | H | OCH₃ | Cl | CH | |
| 249 | —(CH₂)₅— | | C₂H₅ | H | H | CH₃ | CH₃ | CH | |
| 250 | —(CH₂)₅— | | C₂H₅ | H | H | OCH₃ | OCH₃ | N | |
| 251 | —(CH₂)₂O(CH₂)₂— | | CH₃ | H | H | OCH₃ | Cl | CH | |
| 252 | —(CH₂)₂O(CH₂)₂— | | CH₃ | H | H | CH₃ | CH₃ | CH | |
| 253 | —(CH₂)₂O(CH₂)₂— | | CH₃ | H | H | OCH₃ | OCH₃ | N | |
| 254 | —(CH₂)₂O(CH₂)₂— | | C₂H₅ | H | H | OCH₃ | Cl | CH | |
| 255 | —(CH₂)₂O(CH₂)₂— | | C₂H₅ | H | H | CH₃ | CH₃ | CH | |
| 256 | —(CH₂)₂O(CH₂)₂— | | C₂H₅ | H | H | OCH₃ | OCH₃ | N | |
| 257 | CH₃ | OCH₃ | CH₃ | H | H | OCH₃ | Cl | CH | |
| 258 | CH₃ | OCH₃ | CH₃ | H | H | CH₃ | CH₃ | CH | |
| 259 | CH₃ | OCH₃ | CH₃ | H | H | OCH₃ | OCH₃ | N | |
| 260 | CH₃ | OCH₃ | C₂H₅ | H | H | OCH₃ | Cl | CH | |
| 261 | CH₃ | OCH₃ | C₂H₅ | H | H | CH₃ | CH₃ | CH | |
| 262 | CH₃ | OCH₃ | C₂H₅ | H | H | OCH₃ | OCH₃ | N | |
| 263 | CH₃ | C₆H₅ | CH₃ | H | H | OCH₃ | Cl | CH | |
| 264 | CH₃ | C₆H₅ | CH₃ | H | H | CH₃ | CH₃ | CH | |
| 265 | CH₃ | C₆H₅ | CH₃ | H | H | OCH₃ | OCH₃ | N | |
| 266 | CH₃ | C₆H₅ | C₂H₅ | H | H | OCH₃ | Cl | CH | |
| 267 | CH₃ | C₆H₅ | C₂H₅ | H | H | CH₃ | CH₃ | CH | |

TABLE 2-continued

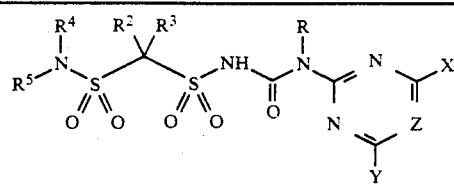

| Compound No. | R⁴ | R⁵ | R² | R³ | R | X | Y | Z | M.p. [°C.] |
|---|---|---|---|---|---|---|---|---|---|
| 268 | CH₃ | C₆H₅ | C₂H₅ | H | H | OCH₃ | OCH₃ | N | |
| 269 | Allyl | Allyl | CH₃ | H | H | OCH₃ | Cl | CH | |
| 270 | Allyl | Allyl | CH₃ | H | H | CH₃ | CH₃ | CH | |
| 271 | Allyl | Allyl | CH₃ | H | H | OCH₃ | OCH₃ | N | |
| 272 | Allyl | Allyl | C₂H₅ | H | H | OCH₃ | Cl | CH | |
| 273 | Allyl | Allyl | C₂H₅ | H | H | CH₃ | CH₃ | CH | |
| 274 | Allyl | Allyl | C₂H₅ | H | H | OCH₃ | OCH₃ | N | |

TABLE 3

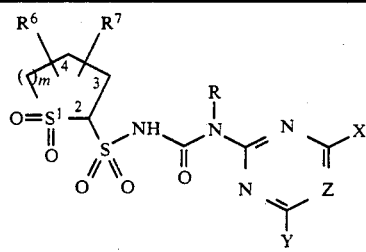

| Compound No. | R⁶ | R⁷ | m | R | X | Y | Z | M.p. [°C.] |
|---|---|---|---|---|---|---|---|---|
| 275 | H | H | 1 | H | OCH₃ | OCH₃ | CH | 208–211 |
| 276 | H | H | 1 | H | OCH₃ | CH₃ | CH | |
| 277 | H | H | 1 | H | CH₃ | CH₃ | CH | |
| 278 | H | H | 1 | H | OCH₃ | Cl | CH | |
| 279 | H | H | 1 | H | OCH₃ | CH₃ | N | |
| 280 | H | H | 1 | H | OCH₃ | OCH₃ | N | |
| 281 | H | H | 1 | H | OCHF₂ | OCH₃ | CH | |
| 282 | H | H | 1 | H | OCHF₂ | OCHF₂ | CH | |
| 283 | H | H | 1 | H | OCH₂CF₃ | OCH₃ | N | |
| 284 | H | H | 1 | H | OC₂H₅ | NHCH₃ | N | |
| 285 | H | H | 1 | H | CH₃ | Cl | CH | |
| 286 | H | H | 1 | H | OC₂H₅ | OC₂H₅ | CH | |
| 287 | H | H | 1 | H | OCH₃ | Br | CH | |
| 288 | H | H | 1 | H | OCH₃ | SCH₃ | CH | |
| 289 | H | H | 1 | H | OCH₃ | OC₃H₇ | CH | |
| 290 | H | H | 1 | H | OCH₂CF₃ | OCH₃ | CH | |
| 291 | H | H | 1 | H | C₂H₅ | OCH₃ | CH | |
| 292 | H | H | 1 | H | OCH₃ | CH(OCH₃)₂ | CH | |
| 293 | H | H | 1 | CH₃ | OCH₃ | OCH₃ | CH | |
| 294 | H | H | 1 | CH₃ | OCH₃ | CH₃ | N | |
| 295 | H | H | 2 | H | OCH₃ | OCH₃ | CH | |
| 296 | H | H | 2 | H | OCH₃ | CH₃ | CH | |
| 297 | H | H | 2 | H | CH₃ | CH₃ | CH | |
| 298 | H | H | 2 | H | OCH₃ | Cl | CH | |
| 299 | H | H | 2 | H | OCH₃ | CH₃ | N | |
| 300 | H | H | 2 | H | OCH₃ | OCH₃ | N | |
| 301 | H | H | 2 | H | OCHF₂ | OCH₃ | CH | |
| 302 | H | H | 2 | H | OCHF₂ | OCHF₂ | CH | |
| 303 | H | H | 2 | H | OCH₂CF₃ | OCH₃ | N | |
| 304 | H | H | 2 | H | OC₂H₅ | NHCH₃ | N | |
| 305 | H | H | 2 | H | CH₃ | Cl | CH | |
| 306 | H | H | 2 | H | OC₂H₅ | OC₂H₅ | CH | |
| 307 | H | H | 2 | H | OCH₃ | Br | CH | |
| 308 | H | H | 2 | H | OCH₃ | SCH₃ | CH | |
| 309 | H | H | 2 | H | OCH₃ | OC₃H₇ | CH | |
| 310 | H | H | 2 | H | OCH₂CF₃ | OCH₃ | CH | |
| 311 | H | H | 2 | H | C₂H₅ | OCH₃ | CH | |
| 312 | H | H | 2 | H | OCH₃ | CH(OCH₃)₂ | CH | |
| 313 | H | H | 2 | CH₃ | OCH₃ | OCH₃ | CH | |
| 314 | H | H | 2 | CH₃ | OCH₃ | CH₃ | N | |
| 315 | 3-CH₃ | H | 1 | H | OCH₃ | OCH₃ | CH | |
| 316 | 3-CH₃ | H | 1 | H | OCH₃ | CH₃ | CH | |
| 317 | 3-CH₃ | H | 1 | H | OCH₃ | CH₃ | N | |
| 318 | 3-CH₃ | 5-CH₃ | 2 | H | OCH₃ | OCH₃ | CH | |

TABLE 3-continued

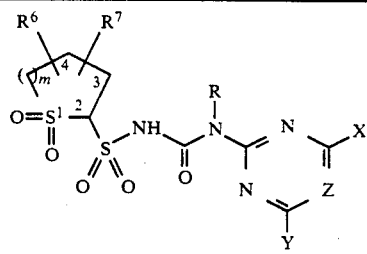

| Compound No. | R⁶ | R⁷ | m | R | X | Y | Z | M.p. [°C.] |
|---|---|---|---|---|---|---|---|---|
| 319 | 3-CH₃ | 5-CH₃ | 2 | H | OCH₃ | CH₃ | CH | |
| 320 | 3-CH₃ | H | 2 | H | OCH₃ | CH₃ | N | |
| 321 | 4-CH₃ | 3-CH₃ | 1 | H | OCH₃ | OCH₃ | CH | |
| 322 | 4-CH₃ | 3-CH₃ | 1 | H | OCH₃ | CH₃ | CH | |
| 323 | 4-CH₃ | H | 1 | H | OCH₃ | CH₃ | N | |
| 324 | 4-CH₃ | H | 2 | H | OCH₃ | OCH₃ | CH | |
| 325 | 4-CH₃ | H | 2 | H | OCH₃ | CH₃ | CH | |
| 326 | 4-CH₃ | H | 2 | H | OCH₃ | CH₃ | N | |
| 327 | 5-CH₃ | 2-CH₃ | 1 | H | OCH₃ | OCH₃ | CH | |
| 328 | 5-CH₃ | 2-CH₃ | 1 | H | OCH₃ | CH₃ | CH | |
| 329 | 5-CH₃ | H | 1 | H | OCH₃ | CH₃ | N | |
| 330 | 5-CH₃ | H | 2 | H | OCH₃ | OCH₃ | CH | |
| 331 | 5-CH₃ | H | 2 | H | OCH₃ | CH₃ | CH | |
| 332 | 5-CH₃ | H | 2 | H | OCH₃ | CH₃ | N | |
| 333 | 6-CH₃ | 2-CH₃ | 2 | H | OCH₃ | OCH₃ | CH | |
| 334 | 6-CH₃ | 2-CH₃ | 2 | H | OCH₃ | CH₃ | CH | |
| 335 | 6-CH₃ | H | 2 | H | OCH₃ | CH₃ | N | |
| 336 | 3-C₂H₅ | H | 1 | H | OCH₃ | OCH₃ | CH | |
| 337 | 4-C₂H₅ | H | 1 | H | OCH₃ | CH₃ | CH | |
| 338 | 5-C₄H₉ | H | 1 | H | OCH₃ | CH₃ | N | |
| 339 | 3-CH₃ | 4-CH₃ | 2 | H | OCH₃ | OCH₃ | CH | |
| 340 | 3-CH₃ | 5-C₂H₅ | 2 | H | OCH₃ | CH₃ | CH | |
| 341 | 3-CH₃ | 6-CH₃ | 2 | H | OCH₃ | CH₃ | N | |

TABLE 4

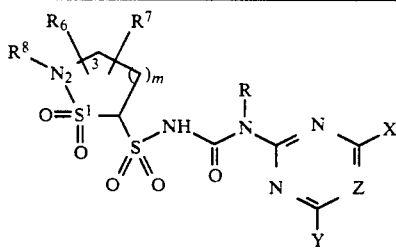

| Compound No. | R⁶ | R⁷ | R⁸ | m | R | X | Y | Z | M.p. [°C.] |
|---|---|---|---|---|---|---|---|---|---|
| 342 | H | H | CH₃ | 1 | H | OCH₃ | OCH₃ | CH | 194 |
| 343 | H | H | CH₃ | 1 | H | OCH₃ | CH₃ | CH | 187 (D.) |
| 344 | H | H | CH₃ | 1 | H | CH₃ | CH₃ | CH | |
| 345 | H | H | CH₃ | 1 | H | OCH₃ | Cl | CH | |
| 346 | H | H | CH₃ | 1 | H | OCH₃ | CH₃ | N | |
| 347 | H | H | CH₃ | 1 | H | OCH₃ | OCH₃ | N | |
| 348 | H | H | CH₃ | 1 | H | OCHF₂ | OCH₃ | CH | |
| 349 | H | H | CH₃ | 1 | H | OCHF₂ | OCHF₂ | CH | |
| 350 | H | H | CH₃ | 1 | H | OCH₂CF₃ | OCH₃ | N | |
| 351 | H | H | CH₃ | 1 | H | OC₂H₅ | NHCH₃ | N | |
| 352 | H | H | CH₃ | 1 | H | CH₃ | Cl | CH | |
| 353 | H | H | CH₃ | 1 | H | OC₂H₅ | OC₂H₅ | CH | |
| 354 | H | H | CH₃ | 1 | H | OCH₃ | Br | CH | |
| 355 | H | H | CH₃ | 1 | H | OCH₃ | SCH₃ | CH | |
| 356 | H | H | CH₃ | 1 | H | OCH₃ | OC₃H₇ | CH | |
| 357 | H | H | CH₃ | 1 | H | OCH₂CF₃ | OCH₃ | CH | |
| 358 | H | H | CH₃ | 1 | H | C₂H₅ | OCH₃ | CH | |
| 359 | H | H | CH₃ | 1 | H | OCH₃ | CH(OCH₃)₂ | CH | |
| 360 | H | H | CH₃ | 1 | CH₃ | OCH₃ | OCH₃ | CH | |
| 361 | H | H | CH₃ | 1 | CH₃ | OCH₃ | CH₃ | N | |
| 362 | H | H | CH₃ | 2 | H | OCH₃ | OCH₃ | CH | 208–209 |
| 363 | H | H | CH₃ | 2 | H | OCH₃ | CH₃ | CH | 180–181 (D.) |
| 364 | H | H | CH₃ | 2 | H | CH₃ | CH₃ | CH | |
| 365 | H | H | CH₃ | 2 | H | OCH₃ | Cl | CH | |
| 366 | H | H | CH₃ | 2 | H | OCH₃ | CH₃ | N | 184–185 |

TABLE 4-continued

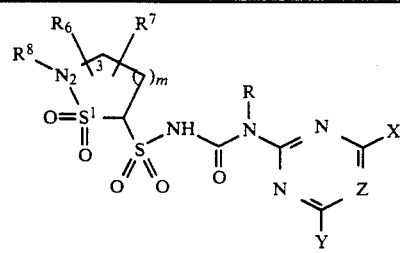

| Compound No. | R⁶ | R⁷ | R⁸ | m | R | X | Y | Z | M.p. [°C.] |
|---|---|---|---|---|---|---|---|---|---|
| 367 | H | H | CH₃ | 2 | H | OCH₃ | OCH₃ | N | |
| 368 | H | H | CH₃ | 2 | H | OCHF₂ | OCH₃ | CH | |
| 369 | H | H | CH₃ | 2 | H | OCHF₂ | OCHF₂ | CH | |
| 370 | H | H | CH₃ | 2 | H | OCH₂CF₃ | OCH₃ | N | |
| 371 | H | H | CH₃ | 2 | H | OC₂H₅ | NHCH₃ | N | |
| 372 | H | H | CH₃ | 2 | H | CH₃ | Cl | CH | |
| 373 | H | H | CH₃ | 2 | H | OC₂H₅ | OC₂H₅ | CH | |
| 374 | H | H | CH₃ | 2 | H | OCH₃ | Br | CH | |
| 375 | H | H | CH₃ | 2 | H | OCH₃ | SCH₃ | CH | |
| 376 | H | H | CH₃ | 2 | H | OCH₃ | OC₃H₇ | CH | |
| 377 | H | H | CH₃ | 2 | H | OCH₂CF₃ | OCH₃ | CH | |
| 378 | H | H | CH₃ | 2 | H | C₂H₅ | OCH₃ | CH | |
| 379 | H | H | CH₃ | 2 | H | OCH₃ | CH(OCH₃)₂ | CH | |
| 380 | H | H | CH₃ | 2 | CH₃ | OCH₃ | OCH₃ | CH | |
| 381 | H | H | CH₃ | 2 | CH₃ | OCH₃ | CH₃ | N | |
| 382 | H | H | C₂H₅ | 1 | H | OCH₃ | OCH₃ | CH | |
| 383 | H | H | C₂H₅ | 1 | H | OCH₃ | CH₃ | CH | |
| 384 | H | H | C₂H₅ | 1 | H | OCH₃ | CH₃ | N | |
| 385 | H | H | CH(CH₃)₂ | 1 | H | OCH₃ | OCH₃ | CH | |
| 386 | H | H | CH(CH₃)₂ | 1 | H | OCH₃ | CH₃ | CH | |
| 387 | H | H | CH(CH₃)₂ | 1 | H | OCH₃ | CH₃ | N | |
| 388 | H | H | C₄H₉ | 1 | H | OCH₃ | OCH₃ | CH | |
| 389 | H | H | C₄H₉ | 1 | H | OCH₃ | CH₃ | CH | |
| 390 | H | H | C₄H₉ | 1 | H | OCH₃ | CH₃ | N | |
| 391 | H | H | CH₂CH=CH₂ | 1 | H | OCH₃ | OCH₃ | CH | |
| 392 | H | H | CH₂CH=CH₂ | 1 | H | OCH₃ | CH₃ | CH | |
| 393 | H | H | CH₂CH=CH₂ | 1 | H | OCH₃ | CH₃ | N | |
| 394 | H | H | CH₂C≡CH | 1 | H | OCH₃ | OCH₃ | CH | |
| 395 | H | H | CH₂C≡CH | 1 | H | OCH₃ | CH₃ | CH | |
| 396 | H | H | CH₂C≡CH | 1 | H | OCH₃ | CH₃ | N | |
| 397 | H | H | OCH₃ | 1 | H | OCH₃ | OCH₃ | CH | |
| 398 | H | H | OCH₃ | 1 | H | OCH₃ | CH₃ | CH | |
| 399 | H | H | OCH₃ | 1 | H | OCH₃ | CH₃ | N | |
| 400 | H | H | N(CH₃)₂ | 1 | H | OCH₃ | OCH₃ | CH | |
| 401 | H | H | N(CH₃)₂ | 1 | H | OCH₃ | CH₃ | CH | |
| 402 | H | H | N(CH₃)₂ | 1 | H | OCH₃ | CH₃ | N | |
| 403 | H | H | CH₂CH₂OCH₃ | 1 | H | OCH₃ | OCH₃ | CH | |
| 404 | H | H | CH₂CH₂OCH₃ | 1 | H | OCH₃ | CH₃ | CH | |
| 405 | H | H | CH₂CH₂OCH₃ | 1 | H | OCH₃ | CH₃ | N | |
| 406 | H | H | CH₂CO₂CH₃ | 1 | H | OCH₃ | OCH₃ | CH | |
| 407 | H | H | CH₂CO₂CH₃ | 1 | H | OCH₃ | CH₃ | CH | |
| 408 | H | H | CH₂CO₂CH₃ | 1 | H | OCH₃ | CH₃ | N | |
| 409 | H | H | C₂H₅ | 2 | H | OCH₃ | OCH₃ | CH | |
| 410 | H | H | C₂H₅ | 2 | H | OCH₃ | CH₃ | CH | |
| 411 | H | H | C₂H₅ | 2 | H | OCH₃ | CH₃ | N | |
| 412 | H | H | CH(CH₃)₂ | 2 | H | OCH₃ | OCH₃ | CH | |
| 413 | H | H | CH(CH₃)₂ | 2 | H | OCH₃ | CH₃ | CH | |
| 414 | H | H | CH(CH₃)₂ | 2 | H | OCH₃ | CH₃ | N | |
| 415 | H | H | C₄H₉ | 2 | H | OCH₃ | OCH₃ | CH | |
| 416 | H | H | C₄H₉ | 2 | H | OCH₃ | CH₃ | CH | |
| 417 | H | H | C₄H₉ | 2 | H | OCH₃ | CH₃ | N | |
| 418 | H | H | CH₂CH=CH₂ | 2 | H | OCH₃ | OCH₃ | CH | |
| 419 | H | H | CH₂CH=CH₂ | 2 | H | OCH₃ | CH₃ | CH | |
| 420 | H | H | CH₂CH=CH₂ | 2 | H | OCH₃ | CH₃ | N | |
| 421 | H | H | CH₂C≡CH | 2 | H | OCH₃ | OCH₃ | CH | |
| 422 | H | H | CH₂C≡CH | 2 | H | OCH₃ | CH₃ | CH | |
| 423 | H | H | CH₂C≡CH | 2 | H | OCH₃ | CH₃ | N | |
| 424 | H | H | OCH₃ | 2 | H | OCH₃ | OCH₃ | CH | |
| 425 | H | H | OCH₃ | 2 | H | OCH₃ | CH₃ | CH | |
| 426 | H | H | OCH₃ | 2 | H | OCH₃ | CH₃ | N | |
| 427 | H | H | N(CH₃)₂ | 2 | H | OCH₃ | OCH₃ | CH | |
| 428 | H | H | N(CH₃)₂ | 2 | H | OCH₃ | CH₃ | CH | |
| 429 | H | H | N(CH₃)₂ | 2 | H | OCH₃ | CH₃ | N | |
| 430 | H | H | CH₂CH₂OCH₃ | 2 | H | OCH₃ | OCH₃ | CH | |
| 431 | H | H | CH₂CH₂OCH₃ | 2 | H | OCH₃ | CH₃ | CH | |
| 432 | H | H | CH₂CH₂OCH₃ | 2 | H | OCH₃ | CH₃ | N | |
| 433 | H | H | CH₂CO₂CH₃ | 2 | H | OCH₃ | OCH₃ | CH | |

TABLE 4-continued

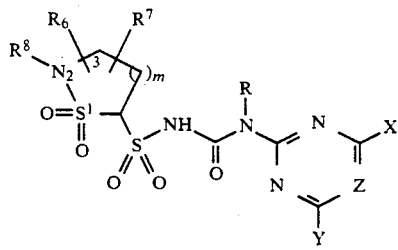

| Compound No. | R6 | R7 | R8 | m | R | X | Y | Z | M.p. [°C.] |
|---|---|---|---|---|---|---|---|---|---|
| 434 | H | H | CH2CO2CH3 | 2 | H | OCH3 | CH3 | CH | |
| 435 | H | H | CH2CO2CH3 | 2 | H | OCH3 | CH3 | N | |
| 436 | 3-CH3 | H | CH3 | 1 | H | OCH3 | OCH3 | CH | |
| 437 | 3-CH3 | H | CH3 | 1 | H | OCH3 | CH3 | CH | |
| 438 | 3-CH3 | H | CH3 | 1 | H | OCH3 | CH3 | N | |
| 439 | 3-CH3 | H | CH3 | 2 | H | OCH3 | OCH3 | CH | |
| 440 | 3-CH3 | H | CH3 | 2 | H | OCH3 | CH3 | CH | |
| 441 | 3-CH3 | H | CH3 | 2 | H | OCH3 | CH3 | N | |
| 442 | 4-CH3 | H | CH3 | 1 | H | OCH3 | OCH3 | CH | |
| 443 | 4-CH3 | H | CH3 | 1 | H | OCH3 | CH3 | CH | |
| 444 | 4-CH3 | H | CH3 | 1 | H | OCH3 | CH3 | N | |
| 445 | 4-CH3 | H | CH3 | 2 | H | OCH3 | OCH3 | CH | |
| 446 | 4-CH3 | H | CH3 | 2 | H | OCH3 | CH3 | CH | |
| 447 | 4-CH3 | H | CH3 | 2 | H | OCH3 | CH3 | N | |
| 448 | 5-CH3 | H | CH3 | 1 | H | OCH3 | OCH3 | CH | |
| 449 | 5-CH3 | H | CH3 | 1 | H | OCH3 | CH3 | CH | |
| 450 | 5-CH3 | H | CH3 | 1 | H | OCH3 | CH3 | N | |
| 451 | 5-CH3 | H | CH3 | 2 | H | OCH3 | OCH3 | CH | |
| 452 | 5-CH3 | H | CH3 | 2 | H | OCH3 | CH3 | CH | |
| 453 | 5-CH3 | H | CH3 | 2 | H | OCH3 | CH3 | N | |
| 454 | 6-CH3 | H | CH3 | 2 | H | OCH3 | OCH3 | CH | |
| 455 | 6-CH3 | H | CH3 | 2 | H | OCH3 | CH3 | CH | |
| 456 | 6-CH3 | H | CH3 | 2 | H | OCH3 | CH3 | N | |
| 457 | 3-CH3 | 4-CH3 | CH3 | 1 | H | OCH3 | OCH3 | CH | |
| 458 | 3-CH3 | 5-CH3 | CH3 | 1 | H | OCH3 | CH3 | CH | |
| 459 | 3-CH3 | 4-C2H5 | CH3 | 1 | H | OCH3 | CH3 | N | |
| 460 | 3-CH3 | 4-C4H9 | CH3 | 2 | H | OCH3 | OCH3 | CH | |
| 461 | 3-CH3 | 5-CH3 | CH3 | 2 | H | OCH3 | CH3 | CH | |
| 462 | 3-CH3 | 6-CH3 | CH3 | 2 | H | OCH3 | CH3 | N | |
| 463 | 4-CH3 | 3-C2H5 | CH3 | 1 | H | OCH3 | OCH3 | CH | |
| 464 | 4-CH3 | 3-C3H7 | CH3 | 1 | H | OCH3 | CH3 | CH | |
| 465 | 4-CH3 | 3-C4H9 | CH3 | 1 | H | OCH3 | CH3 | N | |
| 466 | 4-CH3 | 3-CH3 | CH3 | 2 | H | OCH3 | OCH3 | CH | |
| 467 | 4-CH3 | 5-CH3 | CH3 | 2 | H | OCH3 | CH3 | CH | |
| 468 | 4-CH3 | 6-CH3 | CH3 | 2 | H | OCH3 | CH3 | N | |
| 469 | 5-CH3 | 5-CH3 | CH3 | 2 | H | OCH3 | OCH3 | CH | |
| 470 | 5-CH3 | 6-CH3 | CH3 | 2 | H | OCH3 | CH3 | CH | |
| 471 | 5-CH3 | 3-C4H9 | CH3 | 2 | H | OCH3 | CH3 | N | |

TABLE 5

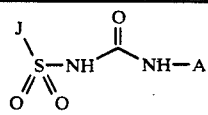

| Compound No. | J | A |
|---|---|---|
| 472 | | |

TABLE 5-continued

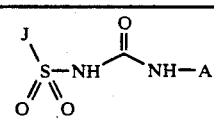

| Compound No. | J | A |
|---|---|---|
| 473 | | |

TABLE 5-continued

J-SO₂-NH-CO-NH-A

| Compound No. | J | A |
|---|---|---|
| 474 | 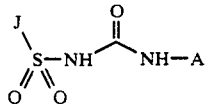 | 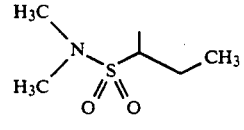 |
| 475 | 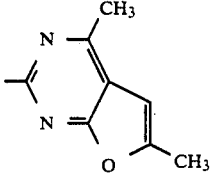 | 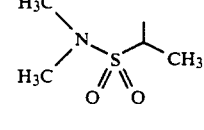 |
| 476 | 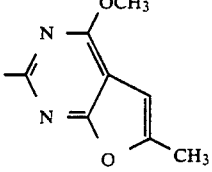 | 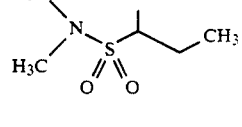 |
| 477 | 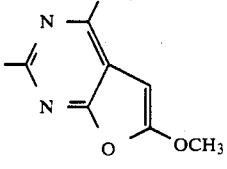 | 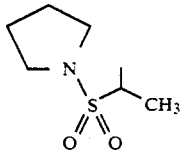 |
| 478 | 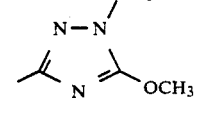 | 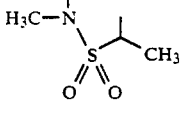 |
| 479 | 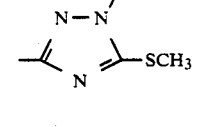 | 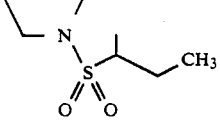 |
| 480 | 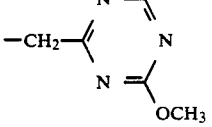 | 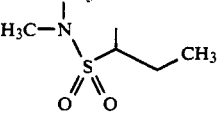 |
| 481 | 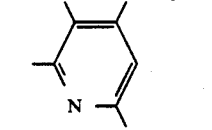 | 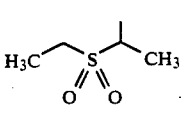 |
| 482 | 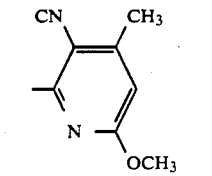 | 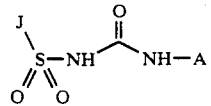 |
| 483 | 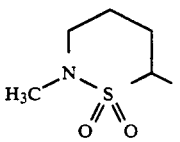 | 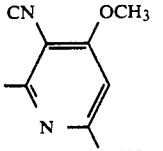 |
| 484 | 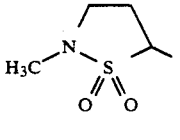 | 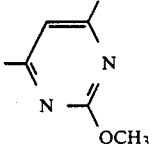 |

TABLE 6

J-SO₂NH₂

| Compound No. | J | M.p. [°C.] |
|---|---|---|
| 485 | $H_3CSO_2CH_2-$ | |
| 486 | $H_5C_2SO_2CH(CH_3)-$ | |
| 487 | $H_7C_3SO_2CH(C_2H_5)-$ | |
| 488 | $(CH_3)_2NSO_2CH_2-$ | 164–165 |
| 489 | $(CH_3)_2NSO_2CH(CH_3)-$ | |
| 490 | $(CH_3)_2NSO_2CH(C_2H_5)-$ | |
| 491 | $(CH_3)_2NSO_2CH(C_3H_7)-$ | 107–108 |
| 492 | $(CH_3)_2NSO_2C(CH_3)_2-$ | 122 |
| 493 | $(CH_3)_2NSO_2CH(C_6H_5)-$ | |
| 494 | Pyrrolidino-$SO_2CH(CH_3)-$ | 123–124 |
| 495 | Pyrrolidino-$SO_2CH(C_2H_5)-$ | 110–112 |
| 496 | Piperidino-$SO_2CH(CH_3)-$ | 91–92 |
| 497 | Piperidino-$SO_2CH(C_2H_5)-$ | |
| 498 | Morpholino-$SO_2CH(CH_3)-$ | |
| 499 | Morpholino-$SO_2CH(C_2H_5)-$ | |
| 500 | $(Allyl)_2NSO_2CH(CH_3)-$ | |
| 501 | $(Allyl)_2NSO_2CH(C_2H_5)-$ | |
| 502 | $H_3C(H_3CO)NSOCH(CH_3)-$ | |
| 503 | $H_3C(H_3CO)NSO_2CH(C_2H_5)-$ | |
| 504 | $H_3C(C_6H_5)NSO_2CH(CH_3)-$ | |
| 505 | $H_3C(C_6H_5)NSO_2CH(C_2H_5)-$ | |
| 506 | $(C_2H_5)_2NSO_2CH(CH_3)-$ | 105–106 |
| 507 | $(C_2H_5)_2NSO_2CH(C_2H_5)-$ | |
| 508 | 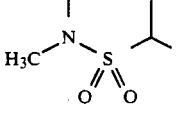 | |
| 509 | 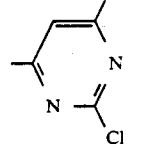 | 121–122 |

TABLE 6-continued

J-SO$_2$NH$_2$

| Compound No. | J | M.p. [°C] |
|---|---|---|
| 510 | H$_3$C-N-S(=O)$_2$ (5-membered ring with methyl substituent) | |
| 511 | H$_3$C-N-S(=O)$_2$ (6-membered ring with methyl substituent) | |
| 512 | H$_3$C-N-S(=O)$_2$ (6-membered ring, N-methyl) | 165 |

FORMULATION EXAMPLES a) A dust is obtained by mixing 10 parts by weight of a compound of the formula (I) and 90 parts by weight of talc as inert substance, and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltauride as wetting and dispersing agent, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (Triton® X207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexane as solvent and 10 parts by weight of oxyethylated nonylphenol as emulsifier.

e) Water-dispersible granules are obtained by mixing
75 parts by weight of a compound of the formula (I),
10 parts by weight of calcium ligninsulfonate,
5 l parts by weight of sodium lauryl sulfate,
3 parts by weight of polyvinyl alcohol and
7 parts by weight of kaolin,
grinding the powder on a pinned-disk mill, and granulating the powder in a fluidized bed by spraying on water as granulation liquid.

f) Water-dispersible granules are also obtained by homogenizing and precomminuting
25 parts by weight of a compound of the formula (I),
5 parts by weight of sodium 2,2'-dinaphthylmethane-6,6'-disulfonate,
2 parts by weight of sodium oleoylmethyltaurinate,
1 parts by weight of polyvinyl alcohol,
17 parts by weight of calcium carbonate and
50 parts by weight of water
on a colloid mill, subsequently grinding the mixture on a bead mill, and atomizing and drying the resulting suspension in a spray tower by means of a single-fluid nozzle.

g) Extruder granules are obtained by mixing 20 parts by weight of active substance, 3 parts by weight of sodium ligninsulfonate, 1 part by weight of carboxymethylcellulose and 76 parts by weight of kaolin, grinding the mixture and moistening it with water. This mixture is extruded and subsequently dried in a stream of air.

BIOLOGICAL EXAMPLES

The damage to the weed plants, or the tolerance by the crop plants, was scored using a key in which the effectiveness is expressed by figures from 0 to 5. The figures denote:

0 = no effect
1 = 0 to 20% effect or damage
2 = 20 to 40% effect or damage
3 = 50 to 60% effect or damage
4 = 60 to 80% effect or damage
5 = 80 to 100% effect or damage

1. Pre-emergence Effect on Weeds

Seeds or rhizome pieces of monocotyledone and dicotyledon weed plants were placed in sandy loam solid in plastic pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures in Table 7, the compounds according to the invention have a good herbicidal pre-emergence action against a broad range of grass weeds and dicotyledon weeds.

TABLE 7

| Example No. | Dosage rate (kg of a.i./ha) | pre-emergence action Herbicidal action | | | |
|---|---|---|---|---|---|
| | | SIAL | CRSE | STME | ECCR |
| 4 | 0.3 | 5 | 5 | 4 | 3 |
| 9 | 0.3 | 5 | 5 | 5 | 5 |
| 91 | 0.3 | 5 | 5 | 5 | 5 |
| 111 | 0.3 | 5 | 5 | 5 | 5 |

Abbreviations:
SIAL = *Sinapis alba*
CRSE = *Chrysanthemum segetum*
STME = *Stellaria media*
ECCR = *Echinochloa crus-galli*
a.i. = active ingredient

2. Post-emergence Effect on Weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls.

The agents according to the invention also have a good herbicidal post-emergence action against a broad range of economically important grass weeds and dicotyledon weeds (Table 8).

TABLE 8

| Example No. | Dosage rate (kg of a.i./ha) | Post-emergence action Herbicidal action | | | |
|---|---|---|---|---|---|
| | | SIAL | CRSE | STME | ECCR |
| 4 | 0.3 | 5 | 5 | 4 | 4 |
| 9 | 0.3 | 4 | 5 | 4 | 4 |
| 91 | 0.3 | 5 | 5 | 4 | 4 |
| 111 | 0.3 | 5 | 5 | 5 | 5 |

3. Tolerance by Crop Plants

In further greenhouse experiments, seeds of a substantial number of crop plants and weeds were placed in sandy loam soil and covered with soil.

Some of the pots were treated immediately as described under 1., and the remaining pots were placed in a greenhouse until the plants had developed two to three leaves and then sprayed with various dosages of the substances according to the invention, as described under 2.

Visual scoring four to five weeks after the application and after the plants had been in the greenhouse revealed that the compounds according to the invention did not inflict any damage to dicotyledon crops such as, for example, soya, cotton, oilseed rape, sugar beet and potatoes when used pre- and post-emergence, even when high dosages of active substance were used. Moreover, some substances also left Gramineae crops such as, for example, barley, wheat rye, Sorghum species, maize or rice unharmed. The compounds of the formula (I) therefore have a high selectivity when used for controlling undesired plant growth in agricultural crops.

We claim:

1. A compound of the formula I or salts thereof

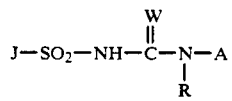

in which J is a radical of the formula (J-2)

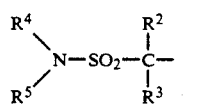

wherein $R^2$ and $R^3$ independently of one another are hydrogen, halogen, $(C_1-C_4)$alkoxy, $(C_1-C_4)$alkylthio, $(C_1-C_6)$alkyl, $(C_2-C_6)$alkenyl, $(C_2-C_6)$alkynyl, the 5 last-mentioned radicals being unsubstituted or monosubstituted or polysubstituted by halogen or monosubstituted or disubstituted by radicals from the group comprising $(C_1-C_4)$alkoxy and $(C_1-C_4)$alkylthio, or are $(C_1-C_4$-alkoxy)carbonyl-$(C_1-C_3)$alkyl, —$(CH_2)_a$—phenyl, a being 0, 1 or 2 and the phenyl radical being unsubstituted or substituted by one or more radicals from the group comprising halogen, $(C_1-C_4)$alkyl, $(C_1-C_4)$alkoxy, $(C_1-C_4$-alkoxy)carbonyl, $(C_1-C_4)$alkylthio and $(C_1-C_4)$alkylsulfonyl, the 5 last-mentioned radicals being unsubstituted in the alkyl moiety or monosubstituted or polysubstituted by halogen;

$R^4$ and $R^5$ independently of one another are hydrogen, $(C_1-C_8)$alkyl, $(C_2-C_8)$alkenyl, $(C_2-C_8)$alkynyl, the 3 last-mentioned radicals being unsubstituted or monosubstituted or polysubstituted by halogen or monosubstituted or disubstituted by $(C_1-C_4)$alkoxy or $(C_1-C_4)$alkylthio, or are $(C_1-C_4$-alkoxycarbonyl$(C_1-C_3)$alkyl, —$(CH_2)_a$-phenyl, a being 0, 1 or 2 and the phenyl radical being unsubstituted or monosubstituted or polysubstituted by radicals from the group comprising halogen, $(C_1-C_4)$alkyl, $(C_1-C_4)$alkoxy, $(C_1-C_4)$alkylthio, $(C_1-C_4)$alkylsulfonyl, the 4 last-mentioned radicals being unsubstituted in the alkyl moiety or monosubstituted or polysubstituted by halogen, and $(C_1-C_4$-alkoxy)carbonyl, or are $(C_1-C_6)$alkoxy or di$(C_1-C_6)$alkylamino, or $R^4$ and $R^5$ together with the N atom linking them are a heterocyclic ring of the formula

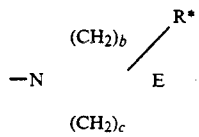

b and c independently of one another being 0, 1, 2 or 3, the total of b+c being the number 3 or 4, $R^*$ being hydrogen, $(C_1-C_4)$alkyl, $(C_1-C_4$-alkoxy)carbonyl or $(C_1-C_4$-alkoxy)methyl and E being a divalent group of the formula O, S, $CH_2$ or N—$(C_1-C_4)$alkyl;

A is a radical of the formula (A-1)

wherein

X and Y independently of one another are H, halogen, $(C_1-C_3)$alkyl, $(C_1-C_3)$alkoxy or $(C_1-C_3)$alkylthio, the 3 last-mentioned alkyl-containing radicals being monosubstituted or polysubstituted by halogen or monosubstituted or disubstituted by $(C_1-C_3)$alkoxy or $(C_1-C_3)$alkylthio, furthermore a radical of the formula $NR^9R^{10}$, $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy;

$R^9$ is hydrogen, $(C_1-C_8)$alkyl, $(C_2-C_8)$alkenyl, $(C_2-C_8)$alkynyl or $(C_1-C_8)$alkoxy, the 4 last-mentioned radicals being unsubstituted or monosubstituted or polysubstituted by halogen or monosubstituted or disubstituted by $(C_1-C_4)$alkoxy or $(C_1-C_4)$alkylthio, or is $(C_1-C_4$-alkoxy)carbonyl-$(C_1-C_3)$alkyl;

$R^{10}$ is hydrogen, $(C_1-C_4)$alkyl, $(C_1-C_4$-alkoxy)carbonyl or $(C_1-C_4$-alkoxy)methyl;

Z is CH;
W is O or S; and
R is hydrogen or CH$_3$.

2. The compound or salts thereof, as claimed in claim 1, wherein:
R$^2$ and R$^3$ independently of one another are hydrogen, (C$_1$-C$_4$)alkyl or (C$_2$-C$_4$)alkenyl;
R$^4$ and R$^5$ independently of one another are hydrogen, (C$_1$-C$_4$)alkyl, (C$_1$-C$_4$)alkoxy or (C$_2$-C$_4$)alkenyl; or
R$^4$ and R$^5$ together are a heterocyclic radical of the formula

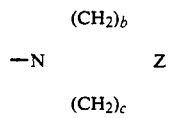

b and c independently of one another being 0, 1, 2 or 3, the total of b+c being the number 3 or 4, and Z being O or CH$_2$;
R$^9$ and R$^{10}$ independently of one another are hydrogen or (C$_1$-C$_4$)alkyl;
X and Y independently of one another are halogen, (C$_1$-C$_4$)alkyl or (C$_1$-C$_4$)alkoxy, it being possible for the two last-mentioned radicals to be monosubstituted or polysubstituted by halogen; and
W is an oxygen atom.

3. The compound or salts thereof, as claimed in claim 2, wherein:
R$^2$ is hydrogen, (C$_1$-C$_4$alkyl) or (C$_2$-C$_4$)alkenyl;
R$^3$ is hydrogen, ethyl or ethyl;
X is methoxy or methyl; and
Y is methoxy, methyl or chloro.

4. The compound or salts thereof, as claimed in claim 1, wherein:
R$^2$ is hydrogen;
R$^3$ is hydrogen;
R$^4$ is methyl;
R$^5$ is methyl;
X is methoxy; and
Y is methoxy.

5. The compound or salts thereof, as claimed in claim 1, wherein:
R$^2$ is methyl;
R$^3$ is hydrogen;
R$^4$ is methyl;
R$^5$ is methyl;
X is methoxy; and
Y is methoxy.

6. The compound or salts thereof, as claimed in claim 1, wherein:
R$^2$ is propyl;
R$^3$ is hydrogen;
R$^4$ is methyl;
R$^5$ is methyl;
X is methoxy; and
Y is methoxy.

7. The compound or salts thereof, as claimed in claim 1, wherein:
R$^2$ is methyl;
R$^3$ is hydrogen;
R$^4$ is ethyl;
R$^5$ is ethyl;
X is methoxy; and
Y is methoxy.

8. The compound or salts thereof, as claimed in claim 1, wherein:
R$^2$ is ethyl;
R$^3$ is hydrogen;
R$^4$ and R$^5$ are —(CH$_2$)$_4$—;
X is methoxy; and
Y is methoxy.

9. The compound or salts thereof, as claimed in claim 1, wherein:
R$^2$ is methyl;
R$^3$ is hydrogen;
R$^4$ and R$^5$ are —(CH$_2$)$_6$—;
X is methoxy; and
Y is methoxy.

10. The compound or salts thereof, as claimed in claim 1, wherein:
R$^2$ is methyl;
R$^3$ is hydrogen;
R$^4$ and R$^5$ are —(CH$_2$)$_5$—;
X is methyl; and
Y is methyl.

11. A compound and salts thereof, as claimed in claim 1, wherein
R is H;
R$^2$ is C$_2$H$_5$;
R$^3$ is H;
R$^4$ and R$^5$ are CH$_3$;
W is O;
X and Y are —OCH$_3$; and
Z is CH.

12. A herbicidal or plant-growth-regulating agent, which contains a compound of the formula (I) or a salt thereof, as claimed in claim 1 in addition to customary formulation auxiliaries.

13. A method of selectively controlling harmful plants, or of regulating the growth of plants, which comprises applying an effective amount of a compound or salts thereof, as defined in claim 1, to the plants, seeds of the plants, or the area on which they grow.

* * * * *

UNITED STATES PATENT AND TRADEMARK OFFICE
CERTIFICATE OF CORRECTION

PATENT NO. : 5,223,017
DATED : June 29, 1993
INVENTOR(S) : Kehne et al.

It is certified that error appears in the above-identified patent and that said Letters Patent is hereby corrected as shown below:

Column 5, lines 1-7, replace "
$$-N\begin{matrix}(CH_2)_b\\ \\(CH_2)_c\end{matrix}\diagup\begin{matrix}R^*\\E\end{matrix}$$
" with " 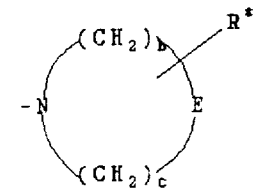 ";

Column 6, lines 4-10, replace "
$$-N\begin{matrix}(CH_2)_b\\ \\(CH_2)_c\end{matrix}\quad Z$$
" with " 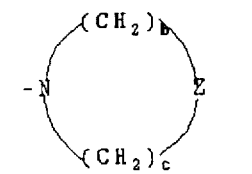 ";

Column 31, line 55, after "5" delete "1";

UNITED STATES PATENT AND TRADEMARK OFFICE
CERTIFICATE OF CORRECTION

PATENT NO. : 5,223,017
DATED : June 29, 1993
INVENTOR(S) : Kehne et al.

It is certified that error appears in the above-identified patent and that said Letters Patent is hereby corrected as shown below:

Column 34, line 26-33, replace "  (CH$_2$)$_b$   R*   " with " 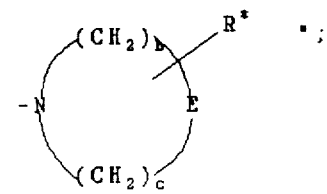";

-N         E (CH$_2$)$_c$

Column 35, lines 13-19, replace "  (CH$_2$)$_b$        " with " 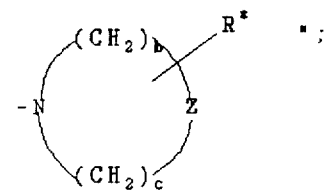";

-N         Z (CH$_2$)$_c$

UNITED STATES PATENT AND TRADEMARK OFFICE
CERTIFICATE OF CORRECTION

PATENT NO. : 5,223,017
DATED : June 29, 1993
INVENTOR(S) : Kehne et al.

It is certified that error appears in the above-identified patent and that said Letters Patent is hereby corrected as shown below:

IN THE CLAIMS:

Claim 9, column 36, line 26, please replace "-$(CH_2)_6$-" with "-$(CH_2)_5$-".

IN THE SPECIFICATION:

Column 13, Compound No. 41 definition $R^2$, replace "$C=CCH_3$" with "$C\equiv CCH_3$";

Column 13, Compound No. 42, definition $R^2$, replace "$C=CCH_3$" with "$C\equiv CCH_3$";

Column 13, Compound No. 43, definition $R^2$, replace "$C=CCH_3$" with "$C\equiv CCH_3$";

Column 13, Compound No. 71, definition $R^1$, replace "$CH_2C=CCH_3$" with "$CH_2C\equiv CCH_3$";

Column 13, Compound No. 72, definition $R^1$, replace "$CH_2C=CCH_3$" with "$CH_2C\equiv CCH_3$";

UNITED STATES PATENT AND TRADEMARK OFFICE
CERTIFICATE OF CORRECTION

PATENT NO. : 5,223,017
DATED : June 29, 1993
INVENTOR(S) : Kehne et al.

It is certified that error appears in the above-identified patent and that said Letters Patent is hereby corrected as shown below:

Column 13, Compound No. 73, definition $R^1$, replace "$CH_2C=CCH_3$" with "$CH_2C\equiv CCH_3$";

Column 17, Compound No. 146, definition $R^2$, replace "$C=CCH_3$" with "$C\equiv CCH_3$";

Column 17, Compound No. 147, definition $R^2$, replace "$C=CCH_3$" with "$C\equiv CCH_3$";

Column 17, Compound No. 148, definition $R^2$, replace "$C=CCH_3$" with "$C\equiv CCH_3$";

Column 25, Compound No. 394, definition $R^8$, replace "$CH_2C=CH$" with $CH_2C\equiv CH$";

UNITED STATES PATENT AND TRADEMARK OFFICE
CERTIFICATE OF CORRECTION

PATENT NO. : 5,223,017
DATED : June 29, 1993
INVENTOR(S) : Kehne et al.

It is certified that error appears in the above-identified patent and that said Letters Patent is hereby corrected as shown below:

Column 25, Compound No. 395, definition $R^8$, replace "$CH_2C=CH$" with "$CH_2C\equiv CH$";

Column 25, Compound No. 396, definition $R^8$, replace "$CH_2C=CH$" with "$CH_2C\equiv CH$";

Column 25, Compound No. 421, definition $R^8$, replace "$CH_2C=CH$" with "$CH_2C\equiv CH$";

Column 25, Compound No. 422, definition $R^8$, replace "$CH_2C=CH$" with "$CH_2C\equiv CH$"; and Column 25, Compound No. 423, definition $R^8$, replace "$CH_2C=CH$" with "$CH_2C\equiv CH$".

Signed and Sealed this

Twelfth Day of July, 1994

Attest:

*Attesting Officer*

BRUCE LEHMAN
*Commissioner of Patents and Trademarks*